US008876761B2

(12) United States Patent
Albrecht et al.

(10) Patent No.: US 8,876,761 B2
(45) Date of Patent: Nov. 4, 2014

(54) INTESTINAL BRAKE INDUCING INTRALUMINAL THERAPEUTIC SUBSTANCE ELUTING DEVICES AND METHODS

(75) Inventors: Thomas E. Albrecht, Cincinnati, OH (US); Jeffrey L. Aldridge, Lebanon, OH (US); Sean P. Conlon, Loveland, OH (US); Michael S. Cropper, Edgewood, KY (US); Denzel Z. Herrera-Davis, Cincinnati, OH (US); Daniel F. Dlugos, Jr., Middletown, OH (US); Jason L. Harris, Mason, OH (US); Christopher J. Hess, Cincinnati, OH (US); Prasanna Malaviya, Mason, OH (US); Glenda C. Marsh, Sao Paulo (BR); Mark S. Ortiz, Milford, OH (US); Mark D. Overmyer, Cincinnati, OH (US); Alessandro Pastorelli, Rome (IT); Galen C. Robertson, Durham, NC (US); Frederick E. Shelton, IV, Hillsboro, OH (US); Michael J. Stokes, Cincinnati, OH (US); James W. Voegele, Cincinnati, OH (US); Lauren S. Weaner, Cincinnati, OH (US); William B. Weisenburgh, II, Maineville, OH (US); Christopher W. Widenhouse, Clarksville, OH (US); Tamara S. Vetro Widenhouse, Clarksville, OH (US); James A. Woodard, Jr., Mason, OH (US); David C. Yates, West Chester, OH (US); Mark S. Zeiner, Mason, OH (US); Andrew M. Zwolinski, Hamburg (DE)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 505 days.

(21) Appl. No.: 13/104,313
(22) Filed: May 10, 2011

(65) Prior Publication Data
US 2011/0295185 A1    Dec. 1, 2011

Related U.S. Application Data

(60) Provisional application No. 61/348,268, filed on May 26, 2010.

(51) Int. Cl.
| A61M 31/00 | (2006.01) |
| A61K 9/00 | (2006.01) |
| A61M 5/142 | (2006.01) |
| A61F 5/00 | (2006.01) |
| A61N 1/05 | (2006.01) |
| A61M 39/02 | (2006.01) |
| A61F 2/04 | (2013.01) |
| A61N 1/36 | (2006.01) |
| A61N 1/372 | (2006.01) |

(52) U.S. Cl.
CPC ............ *A61M 31/002* (2013.01); *A61K 9/0065* (2013.01); *A61M 2210/106* (2013.01); *A61N 1/0509* (2013.01); *A61M 2210/1064* (2013.01); *A61M 5/14276* (2013.01); *A61M 39/0208* (2013.01); *A61F 5/0026* (2013.01); *A61F 2002/045* (2013.01); *A61N 1/36007* (2013.01); *A61F 5/0013* (2013.01); *A61N 1/37205* (2013.01); *A61F 2/04* (2013.01)
USPC ...................................... 604/93.01; 604/500

(58) Field of Classification Search
USPC ............. 604/20, 66, 288.01, 93.01, 180, 500; 607/40; 424/426; 514/558
See application file for complete search history.

(56) References Cited

U.S. PATENT DOCUMENTS

| 7,090,655 | B2 * | 8/2006 | Barry .......................... 604/96.01 |
| 8,162,969 | B2 | 4/2012 | Brister et al. |
| 2005/0131386 | A1 | 6/2005 | Freeman et al. |
| 2007/0178160 | A1 | 8/2007 | Burnett |
| 2007/0293885 | A1 * | 12/2007 | Binmoeller .................... 606/191 |
| 2009/0062717 | A1 * | 3/2009 | Laufer ............................... 604/8 |
| 2009/0311235 | A1 | 12/2009 | Elenko et al. |
| 2010/0312050 | A1 * | 12/2010 | Forsell ............................ 600/37 |

FOREIGN PATENT DOCUMENTS

| WO | WO 2005/074378 | 8/2005 |
| WO | WO 2007/113714 | 10/2007 |

OTHER PUBLICATIONS

Simonian, H.P. et al., "Regional postprandial differences in pH within the stomach and gastroespophageal junction," Digestive Diseases and Sciences, vol. 50(12) (2005) pp. 2276-2285 (Abstract).
International Search Report dated Jul. 3, 2012 for Application No. PCT/US2011/037658.
* cited by examiner

*Primary Examiner* — Kami A Bosworth
*Assistant Examiner* — Imani Hayman
(74) *Attorney, Agent, or Firm* — Frost Brown Todd LLC

(57) ABSTRACT

Methods and devices create an intestinal braking effect, are non-invasive or minimally invasive, and may be reversible. These methods and devices are accomplished via stabilized implantable systems and ingestible pills. In one embodiment, a method of producing satiety comprising the steps of accessing a gastrointestinal tract of a patient and implanting an intraintestinal therapeutic substance eluting implant. The implant is capable of eluting a satiety inducing substance selected from at least one of a nutrient, a specific satiety inducing bio-active substance, pancreatic polypeptides, free fatty acids, cholecystokinin, amino acids, glutamine, lipids, linoleic acid, or a combination thereof, from the implant into the gastrointestinal tract.

19 Claims, 26 Drawing Sheets

INTESTINAL BRAKE INDUCING INTRALUMINAL THERAPEUTIC SUBSTANCE ELUTING DEVICES AND METHODS

PRIORITY

This application claims priority to U.S. Provisional Patent Application Ser. No. 61/348,268, entitled "Intestinal Brake Inducing Intraluminal Therapeutic Substance Eluting Devices and Methods," filed May 26, 2010, the disclosure of which is incorporated by reference herein.

FIELD OF INVENTION

The present invention relates to methods and devices that elute a therapeutic substance which aid in inducing an intestinal braking effect.

BACKGROUND OF THE INVENTION

When food content enters the intestines, an intestinal braking effect occurs which helps to slow the passage of this food content therethrough in order to aid in the absorption of nutrients to in the body. Intestinal brake has been shown to initiate satiation more quickly and is theorized to play an important role in the effectiveness (both Excess Weight Loss (EWL) and comorbidity resolution) of Roux-En-Y Gastric Bypass (RYGB) surgery. Procedures such as ileal transposition have been developed based on the concept of delivery of substances with rich nutrient/caloric content to the ileum and have been shown to be effective in numerous animal models. However, known methods tend to be overly invasive and often require a permanent perforation in the intestinal lumen. Accordingly, there is a need for creating an intestinal braking effect which is non-invasive or minimally invasive, and which may be reversible.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. For example, the features illustrated or described in connection with one exemplary embodiment may be combined with the features of other embodiments. Such modifications and variations are intended to be included within the scope of the present invention.

Figure 1:
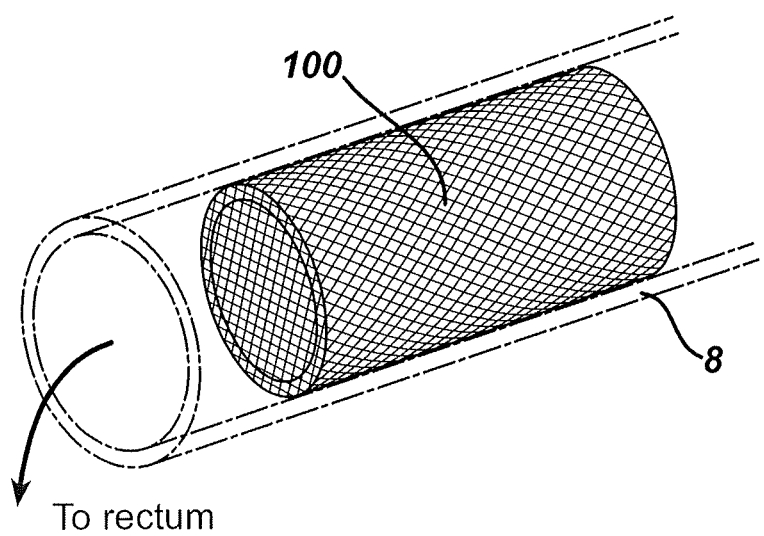
FIG. 1 is a schematic partially transparent view of an intraintestinal therapeutic substance eluting implant.

FIG. 1 is a schematic partially transparent view of an intraintestinal therapeutic substance eluting implant 100. In this particular embodiment, implant 100 is shown as a degradable intestinal stent positioned in intestine 8, just past the ileocecal valve (see reference indicia 10 in FIG. 4). Alternatively, implant 100 may be non-degradable. Implant 100 allows for the addition of nutrients and bio-active substances to the intestines, thereby inducing satiety through an intestinal braking effect. In certain embodiments, implant 100 may be deployed during a standard colonoscopy procedure using a deployment device attached to a flexible endoscope. This device and method would have the benefits of inducing satiety through a non-invasive procedure, and is combinable with the single yearly recommended colonoscopy, thus permitting monitoring of colon health and enabling weight loss in a patient. In one embodiment, implant 100 may be constructed from a degradable polymer having therapeutic substances therein. Non-limiting examples of such therapeutic substances include nutrients and specific satiety inducing bioactive substances such as pancreatic polypeptides (PPY), free fatty acids (FFA) and cholecystokinin (CCK). In alternative embodiments, implant 100 may be coated with bioactive substances such as amino acids, glutamine, or lipids. These substances may elute over time. Implant 100 may be formed from a number of materials including coated string, mesh, fabric, buttons, tube, or any other suitable material. Implant 100 may further be rigid or flexible and may optionally be anchored to the wall of intestine 8 to secure its position. As may be appreciated, implant 100 may be of any desirable shape and size. In certain embodiments, implant 100 may be helically shaped in order to allow flexibility along with intestine 8. Due to the stent shape illustrated in FIG. 1, intestine 8 will begin to grow over implant 100 in time, thereby encapsulating implant 100 in the intestinal wall, thus providing the benefit of direct tissue for the therapeutic substances which would aid in transfer of the therapeutic substances to the bloodstream. In another embodiment, implant 100 may be designed not to adhere to intestine 8. This may be accomplished, for example, by adding a lubricating means to the external surfaces of implant 100. In this manner, implant 100 would be more easily removed from the body should the patient so desire. In the case of implant 100 being a degradable intestinal stent, it may be desirable to construct implant 100 from a polymer or other substance having a full degradation period of a year or so in order to coordinate the full degradation of implant 100 with a yearly colonoscopy, during which a replacement implant 100 may be installed.

In regard to FIG. 1, numerous alternatives are envisioned. For example, in one embodiment, implant 100 may include means to create "pulsations" of therapeutic substances rather than simply providing a constant release of these therapeutic substances. Accordingly, implant 100 may be constructed in a manner which provides alternating layers of therapeutic substance containing polymers and non-therapeutic substance containing polymers. Similarly, the alternating layers may comprise layers containing different dosings or concentrations of the therapeutic substances or different therapeutic substances from the surrounding layers. This may for example create a feeling of satiety, then a reduction in that feeling, or may help maintain the effectiveness of implant 100 through time. Further, the therapeutic substance utilized in implant 100 can be tailored to suit the intended location of the stent, taking into account factors such pH level exposure which may alter the life span of implant 100. Additionally, implant 100 may be configured to deliver an electrical stimulation to the GI tract at a location such as the ileum, and further may elute linoleic acid amongst its therapeutic substances. Non-limiting disclosure of the benefits of electrical stimulation of the ileum in the presence of linoleic acid in order to increase glucagon-like peptide 1 (GLP-1) expression an example of this is disclosed in US2005/0131386A1, Jun. 16, 2005 "METHOD AND DEVICE FOR MINIMALLY INVASIVE IMPLANTATION OF BIOMATERIAL", which is hereby incorporated herein by reference. In yet another embodiment, implant 100 may comprise an intestinal stent containing an active substance such as PPY or GLP-1, and oxytomodulin placed at the ileum. Further, the stent may be in the form of a metal (e.g., cobalt chromium, stainless steel, Nitinol, etc.) or absorbable polymer ring or mesh affixed to the gastrointestinal (GI) tract by sutures. The active substance may be a synthetic which is analogous to a human hormone or animal derived hormone.

The device and procedure outlined herein with respect to FIG. 1 is intended to induce satiety by introducing a therapeutic substance to activate an intestinal braking effect via a therapeutic substance eluting implant 100. The procedure has the further benefit of being non-invasive or minimally invasive, as well as being a reversible procedure should the patient or physician so desire. There are no anatomical changes to the GI tract, and placement of implant 100 may be realized endoluminally via a flexible endoscope or flexible endoscopic platform. Implant 100 may be delivered through a working channel or over the outside of the flexible endoscopic platform. Implant 100 may be delivered in collapsed or expanded state and delivered to the desired location within the GI tract either transorally or transanally. Further, the dosings and concentrations of the therapeutic substance(s) eluted by implant 100 may be tailored to meet the individual needs of the patient and may further be enhanced to vary over time and may be localized to control the delivery of hormone triggers to the desired receptors.

Figure 2:
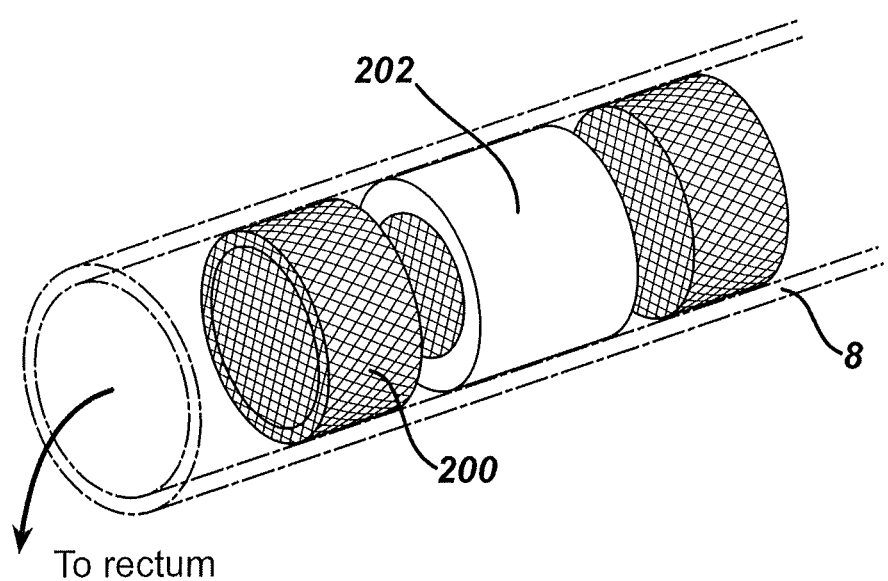
FIG. 2 is schematic partially transparent view of an intraintestinal therapeutic substance eluting implant with a rechargeable drug-eluting reservoir.

FIG. 2 is schematic partially transparent view of an intraintestinal therapeutic substance eluting implant 200 with a rechargeable drug-eluting reservoir 202. In this particular embodiment, therapeutic substance eluting implant 200 is shown as a degradable intestinal stent positioned in intestine 8, just past the ileocecal valve (see reference indicia 10 in FIG. 4), which acts to trap rechargeable drug-eluting reservoir 202 thereon. As with the embodiments disclosed in FIG. 1, this allows for the addition of therapeutic substances such as nutrients and bio-active substances to intestines 8 to induce satiety through an intestinal braking effect. Reservoir 202 may be recharged via an external source, such as through a port fixated to the patient's fascia as is discussed later herein with respect to FIGS. 4 & 5.

Figure 3:
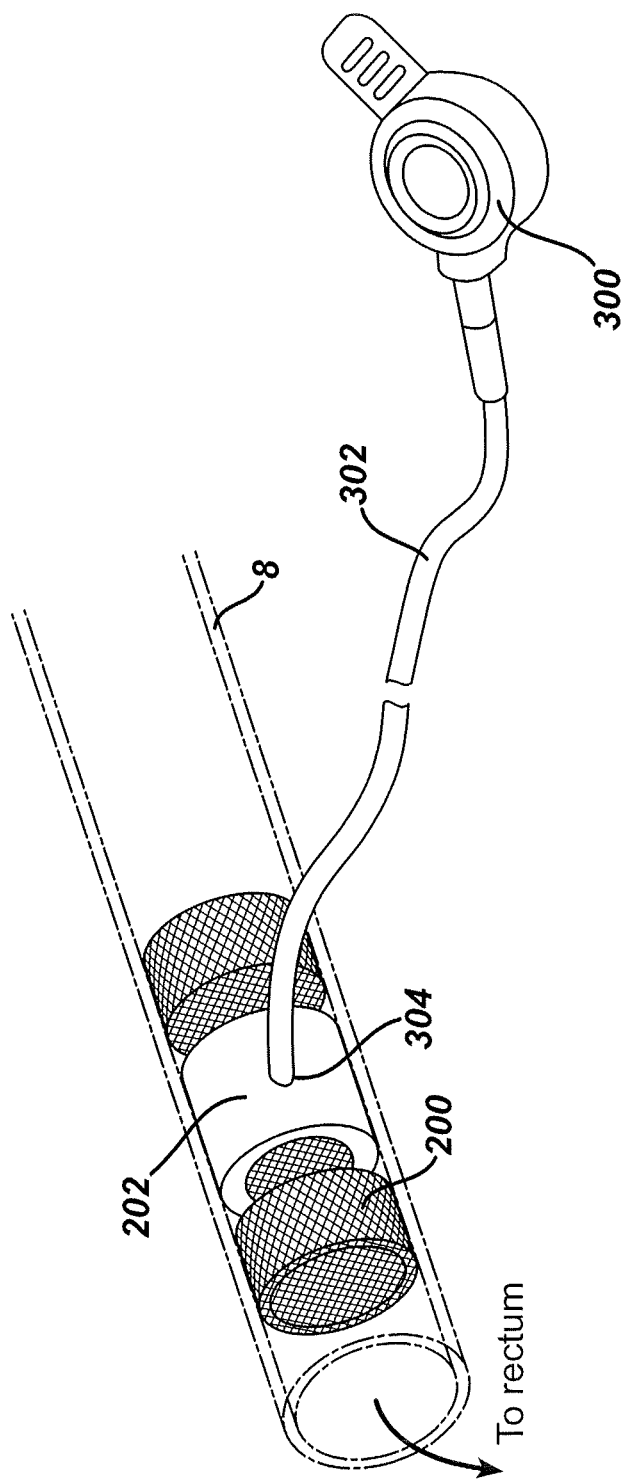
FIG. 3 is a schematic partially transparent view of an intraintestinal therapeutic substance eluting implant with a rechargeable drug-eluting reservoir comprising a fill port attached therewith.

FIG. 3 is a schematic partially transparent view of an intraintestinal therapeutic substance eluting implant 200 with a rechargeable drug-eluting reservoir 202 comprising a fill port 300 attached therewith. In this embodiment, fill port 300 is connected to reservoir 202 via tube 302. In certain embodiments, a valve 304 may be included at the connection point between reservoir 202 and tube 302, or at any other desirable location, in order to maintain a desired fill level of therapeutic substance within reservoir 202. When reservoir 202 falls below the desired fill level, a surgeon may inject additional therapeutic substance into fill port 300 by means such as a Huber needle. Alternatively, a transhepatic catheter may be inserted through hepatic duct 14 (FIG. 4) and pass through liver 2 (FIG. 4), connecting to a subcutaneous fill port 300 for refilling reservoir 202.

Figure 4:
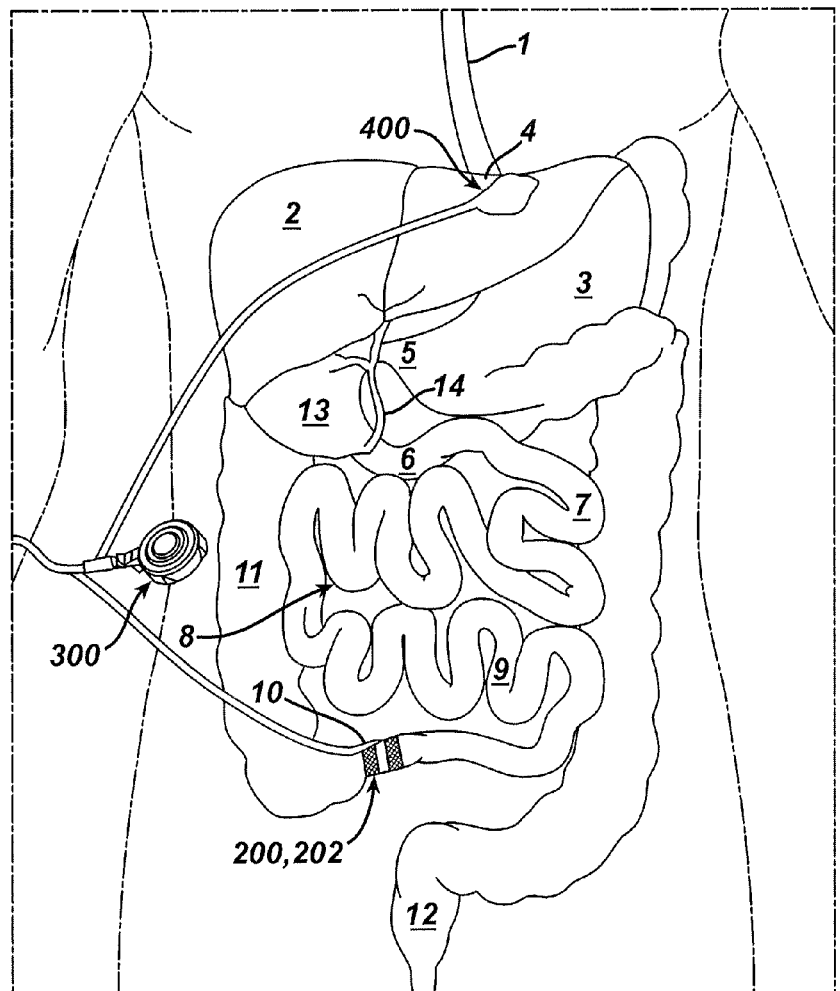
FIG. 4 is a schematic partially transparent view of an intraintestinal therapeutic substance eluting implant with a rechargeable drug-eluting reservoir comprising a fill port and a pressure sensing system attached therewith.

FIG. 4 is a schematic partially transparent view of an intraintestinal therapeutic substance eluting implant 200 with a rechargeable drug-eluting reservoir 202 comprising a fill port 300 and a pressure sensing system 400 attached therewith. In this particular embodiment, the locations of the various components of the system are shown within the body of a patient. Following the natural path through the GI tract, food content enters through esophagus 1 and passes through cardia 4 into stomach 3. After some time, the food content is partially digested and becomes chyme. This chyme exits stomach 3 through pylorus 5 into duodenum 6. Duodenum 6, jejunum 7 and ileum 9 make up the three sections of small intestine 8. At the end of small intestine 8 in the ileum 9 is ileocecal valve 10 which serves to connect small intestine 8 to large intestine 11. Large intestine 11 is the final section of the GI tract and terminates at anus 12 through which solid waste may be expelled from the body. Aiding in the entire digestion process are liver 2 and gall bladder 13 which act to provide bile and other biochemicals necessary for digestion to duodenum 6 through hepatic duct 14. In FIG. 4, a pressure sensing system 400 is positioned at cardia 4 to provide a signal to rechargeable drug-eluting reservoir 202 of intraintestinal therapeutic substance eluting implant 200 when food is consumed. The signal sent initiates activation of a pump (not shown in FIG. 4) which delivers a therapeutic substance through reservoir 202 to induce an intestinal braking effect which would help to create or maintain a sensation of satiety. As has been shown and described previously herein, fill port 300 has been provided to enable the system to be refilled with therapeutic substance when necessary, and may be of the subcutaneous type.

In regard to FIG. 4, numerous alternatives are envisioned. For example, in one embodiment, reservoir 202 may be attached to a micro-pump which would release therapeutic substance automatically at predetermined points during the day in order to induce an intestinal braking effect which would help to create or maintain a sensation of satiety These smaller doses are distributed along a more continuous schedule and serve to maintain the feeling of satiety longer through prolonged addition of nutrients to the lower GI tract. As may be appreciated, additional reservoirs and pumps may be added to the system described above to deliver the desired therapeutic substance. In another embodiment, reservoir 202 may be a degradable therapeutic substance infused foam material that may be injected behind implant 200 to fill the gap created by the shape of implant 200. Over time, the foam material would release the therapeutic substance to induce an intestinal braking effect. This foam material could be re-injected via a flexible member during an annual colonoscopy. In yet another embodiment, reservoir 202 may be constructed from a semi-permeable membrane that would leach out a therapeutic substance over time. Similar to the previous embodiment disclosed, this reservoir could be refilled by means of a flexible member inserted during an annual colonoscopy procedure. For example, the flexible member may comprise a Huber needle at one end which may be attached via tubing to a secondary reservoir, such as a saline bag, external to the patient during the colonoscopy. In still another embodiment, reservoir 202 may comprise a swallowable reservoir that is captured by implant 200. In one embodiment, implant 200 may be in the form of a stent having tines that protrude into intestine 8 and capture reservoir 202 as it is brought into position by the natural peristalsis of the digestive cycle. Reservoir 202 may be in the form of a hollow cylinder which allows chyme to pass therethrough, but contain a therapeutic substance in the reservoir body. The therapeutic substance may then be released via slow perfusion, a small leak or a self-contained pump system. As the therapeutic substance is released, the diameter of reservoir 202 may decrease enough to allow it to pass through implant 200. A replacement reservoir could then be swallowed and the process would repeat.

Figure 5:
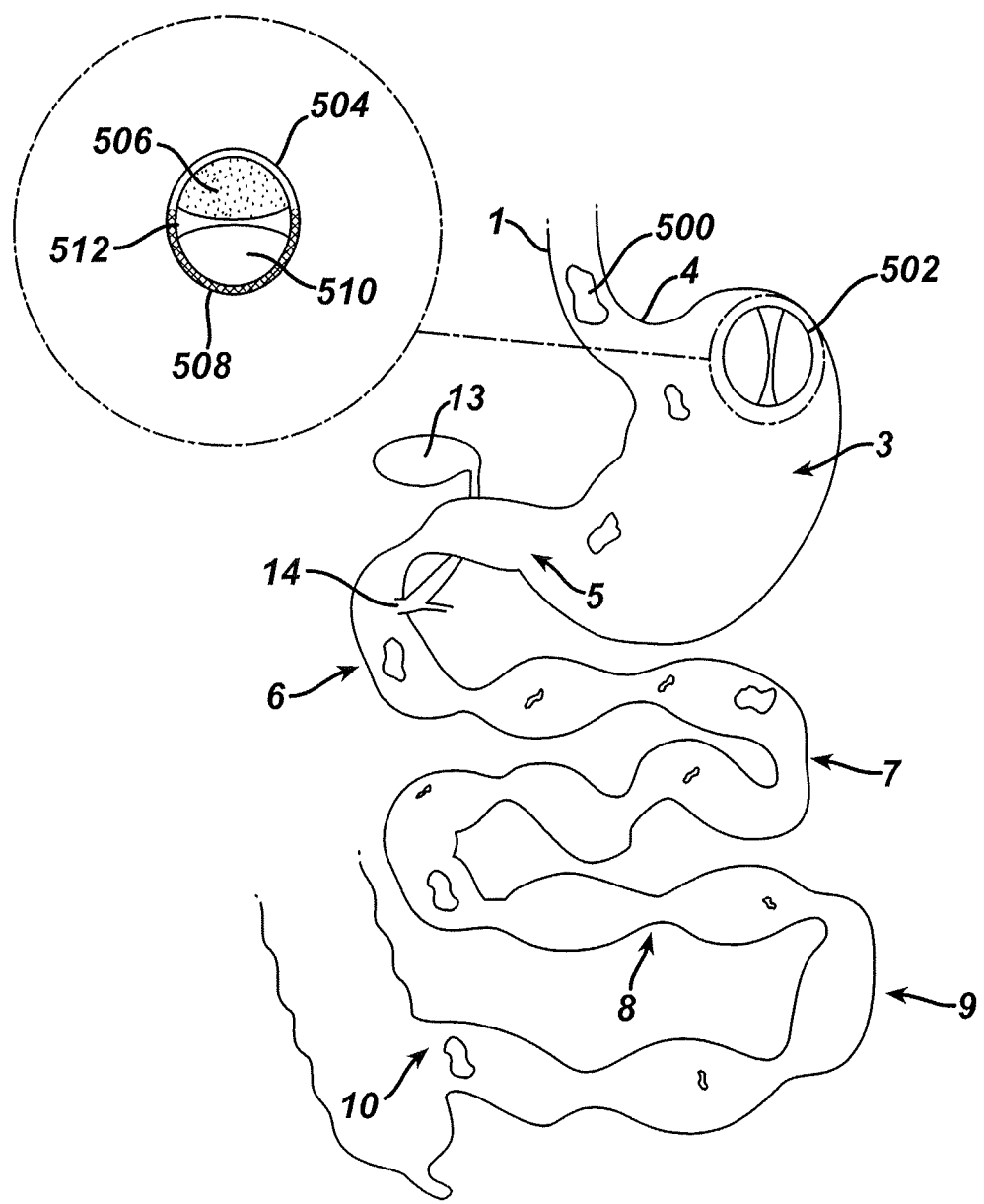
FIG. 5 is a schematic partially transparent view of delivery system for nutrient binding material.

FIG. 5 is a schematic partially transparent view of delivery system for nutrient binding material. As was described previously herein, food content 500 enters the GI tract through esophagus 1 into stomach 3. In this particular embodiment, implant 502 resides within stomach 3. Implant 502 generally comprises a balloon implant that is tacked to the stomach as a long term implant. In one embodiment, implant 502 is divided into two compartments separated by an intermediary wall 512, where one compartment contains a pH sensitive hydrogel 506 and the other compartment contains a non-digestible fatty acid or high soluble fiber liquid 510. Hydrogels are cross-linked hydrophilic polymers that can contain a large amount of water. By incorporating functional groups, a hydrogel can be made stimulus-sensitive, such that they undergo volume changes in response to certain stimuli. Examples of such stimuli include pH changes, temperature changes, light, ion concentrations and electrical fields. In one embodiment where the stimuli is pH change, as a pH level becomes acidic, hydrogel 506 becomes hydrophilic and attracts water through a pH sensitive membrane 504 and begins to expand. As a pH level becomes neutral or basic, hydrogel 506 becomes hydrophobic and contracts, expelling any bound up water through porous membrane 508. When hydrogel 506 is in an expansion mode, not only does membrane 508 allow the entire implant to grow and take up space in the stomach to create a satiety sensation, it also places pressure on the second compartment of implant 502 which contains non-digestible fatty acid or high soluble fiber liquid 510. As the second compartment of implant 502 which contains non-digestible fatty acid or high soluble fiber liquid 510 is placed under pressure by the expansion of hydrogel 506, membrane 508 releases a small amount of the non-digestible fatty acid or high soluble fiber liquid 510 contained therein, which then attaches to food content 500 thereby slowing their absorption into the body as they pass through the remainder of the GI tract. This in turn induces an intestinal brake as undigested nutrients and fatty acids enter ileum 9. Intermediary wall 512 may be constructed of a flexible elastomeric material such as silicone in order to allow a transfer of force from one compartment to the other. In regard to FIG. 5, numerous alternatives are envisioned. For example, in one embodiment, the first compartment may be constructed of a fine mesh or a highly permeable expansible membrane containing hydrogel. Examples of suitable hydrogels include chitosan, polyacrylamide (PAAM), and poly(2-Hydroxyethyl Methacrylate) (pHEMA)).

Figure 6:
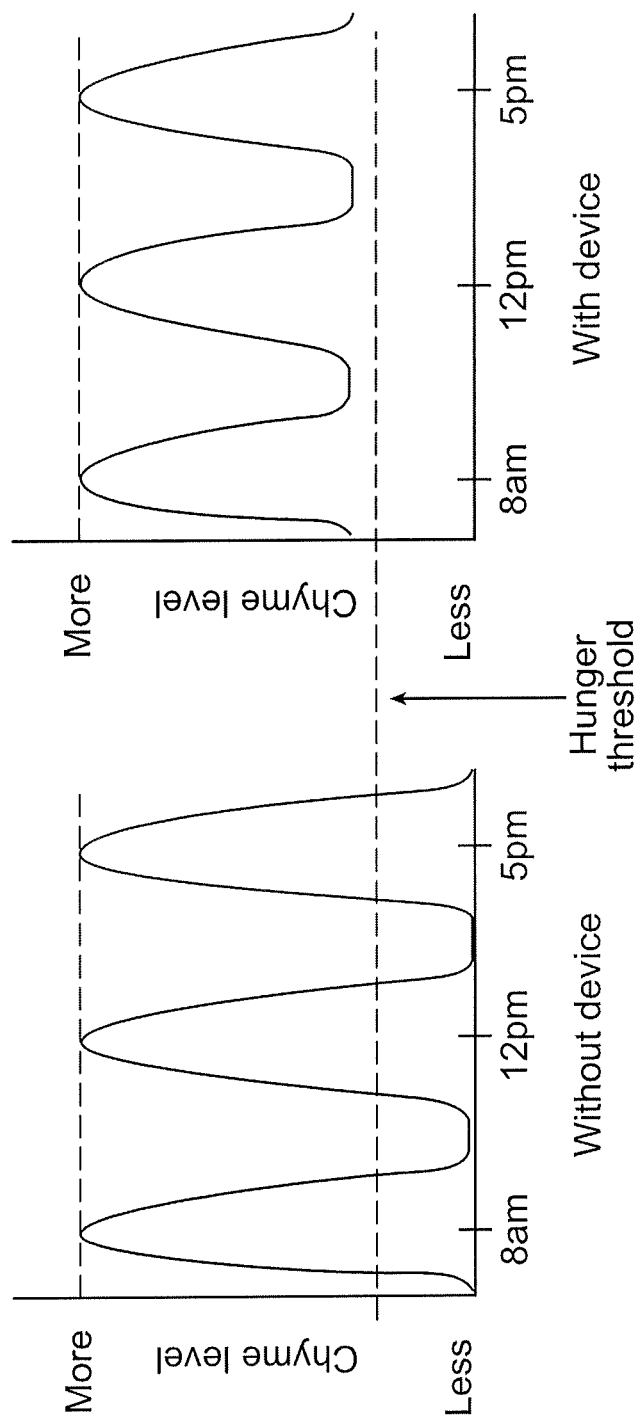
FIG. 6 is a graph representing chyme levels in the body for a patient with and without a chyme holding stent.

In another embodiment a chyme holding implant is provided. FIG. 6 is a graph representing chyme levels in the body for a patient with and without a chyme holding implant. The graph on the left of FIG. 6 illustrates typical chyme levels in the body during the day without a chyme holding stent. As may be appreciated, chyme levels are highest shortly after a meal and decrease over time, eventually crossing the hunger threshold which induces a sensation of hunger in the patient. A more desirable graph is illustrated on the right of FIG. 6 where the chyme levels are maintained above the hunger threshold, thereby maintaining a sensation of satiety in the patient throughout the day. One means for creating such a graph is through the implantation of a chyme holding implant within the intestine which would act to hold a portion of chyme therein to prevent its movement through the intestines, such that chyme is in chemical and/or biological contact with the intestinal cells responsible for intestinal brake, thereby inducing an intestinal braking effect. In one embodiment, chyme would be held long enough so that chyme from one meal would remain into the next. Alternatively, chyme may be held for longer periods of time if so desired. In another embodiment, the implant protects the chyme therein from further digestion through the use of chemical or mechanical means. By holding chyme from one meal to the next, the GI tract would be tricked to behave as if food had just been ingested due to the chyme's tendency to induce the intestinal brake. This would allow the patient to eat less and achieve a desired weight loss.

Figure 7:
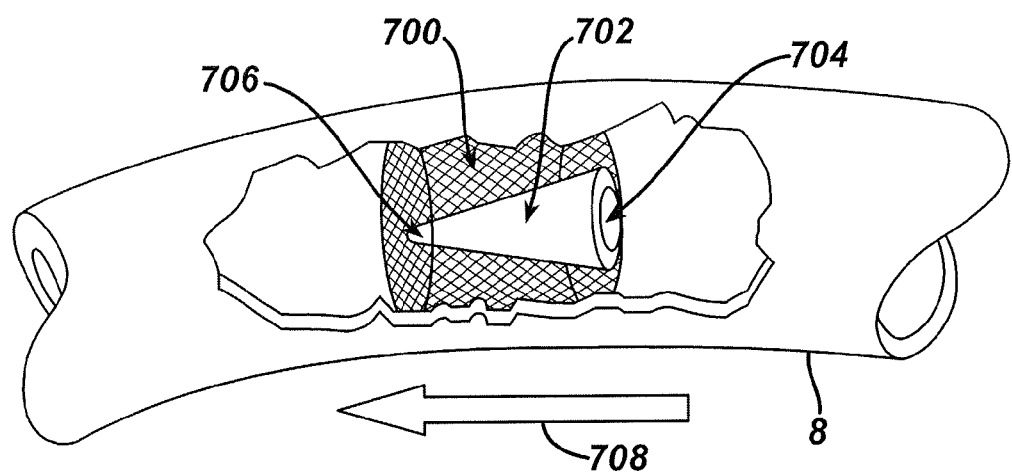
FIG. 7 is a schematic partially transparent view of a collapsible implant with a conical chyme pouch.

FIG. 7 is a schematic partially transparent view of a collapsible implant 700 with a conical, flexible chyme pouch 702 positioned within intestine 8. Implant 700 has an inlet 704 and an outlet 706. Peristalsis forces chyme in the direction indicated by arrow 708 due to narrow exit 706 from pouch 702. Therefore, a select amount of chyme is delayed from movement, which creates a semi-constant stream of chyme between meals, as was discussed previously herein with respect to FIG. 6.

Figure 8A:
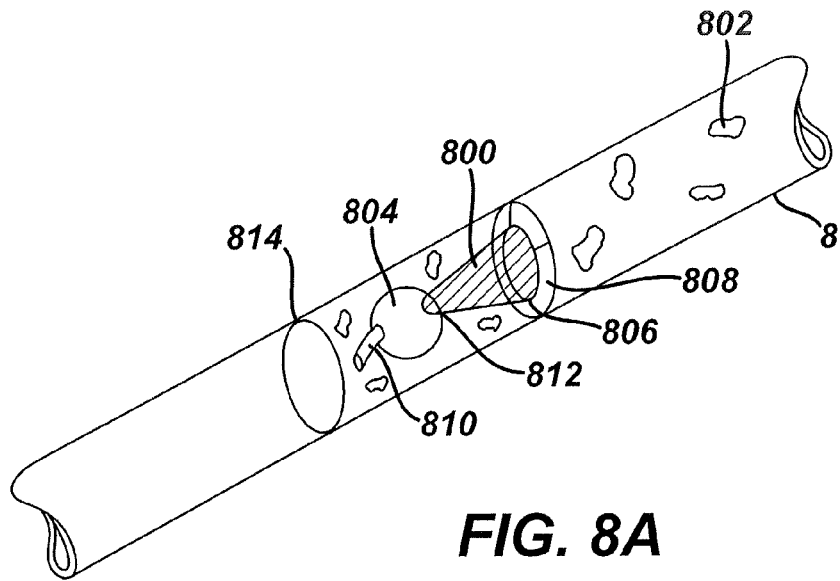
FIG. 8A is a schematic partially transparent view of a chyme holding implant and details thereof.
Figure 8B:
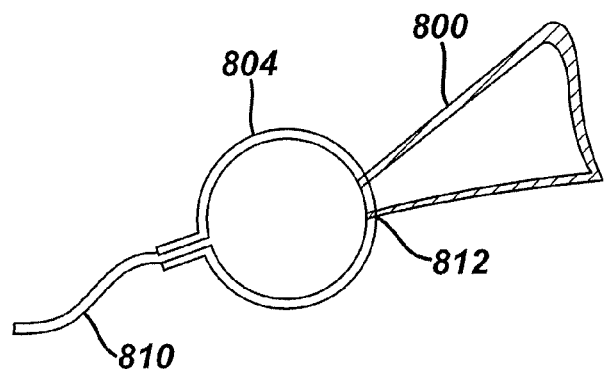
FIG. 8B is a cross-sectional view of an arrangement and interactions of a chyme holding implant.

FIG. 8A is a schematic partially transparent view of a chyme holding implant 800 and details thereof. In the embodiment illustrated in FIG. 8A, chyme 802 may be funneled into an expansible slow leak reservoir 804 to achieve the desired effect of time released chyme. In one embodiment, implant 800 may be suspended by wire elements 806 in intestine 8 which are centered on stent 814 in a configuration that allows some chyme to bypass the reservoir via bypass channels 808 and some to be trapped within reservoir 804. As chyme is accumulated, reservoir 804 would expand. The limited size of slow leak catheter 810 of reservoir 804 would allow the accumulated chyme impelled by the pressure of reservoir 804 returning to its unexpanded state to slowly drip therefrom long after a meal was over. In this manner, chyme may further be prevented from retrograde motion by a one-way valve means at outlet 812, such as a duck bill valve, located between implant 800 and reservoir 804. This increases the capacity of the implant to hold and release chyme, thereby extending the sensation of satiety in the patient. The entire assembly may be located within a stent 814 positioned at a target location within intestine 8. A cross-sectional view of the arrangement and interactions of implant 800, reservoir 804, slow leak catheter 810 and one-way valve 812 are shown in FIG. 8B.

Figure 9:
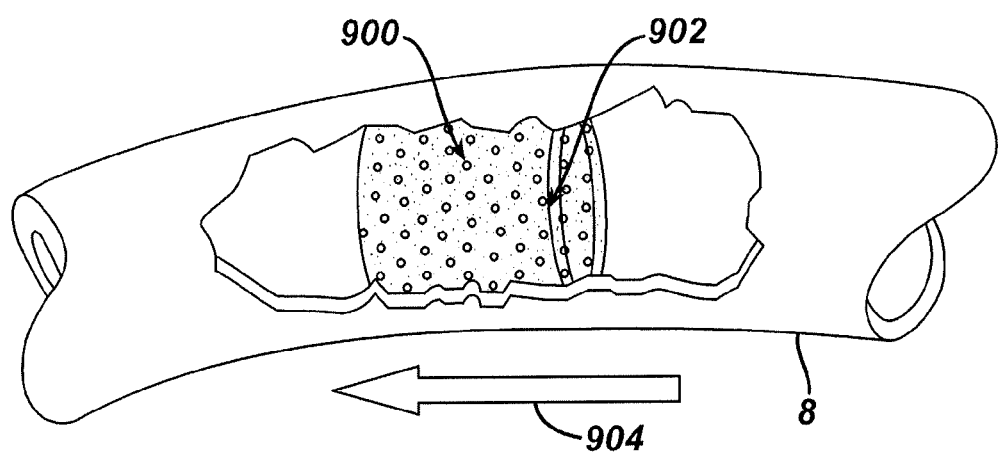
FIG. 9 is a schematic partially transparent view of a collapsible implant with absorbent material.

FIG. 9 is a schematic partially transparent view of a collapsible implant 900 with absorbent material 902. In this particular embodiment, collapsible implant 900 is shown with a piece of absorbent material 902 affixed thereto, and is affixed within intestine 8 at a target location. In one embodiment, material 902 comprises a hollow cylindrical sponge. As peristalsis moves chyme through the GI tract, some chyme contained within material 902 is pushed out, and flows in a direction indicated by arrow 904. Subsequent peristaltic motions repeat this effect. Therefore, some amount of chyme is delayed from movement through the GI tract, thereby creating a prolonged sensation of satiation in a patient.

Figure 10A:
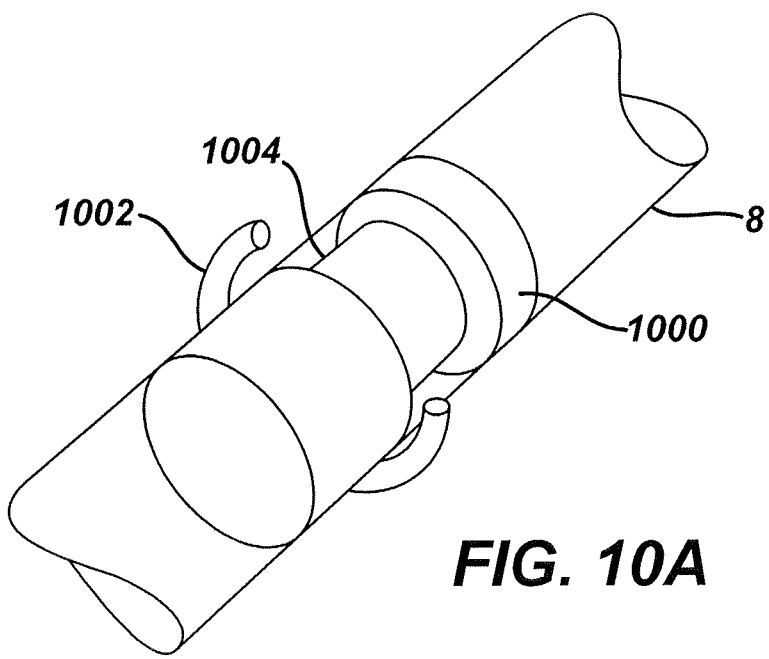
FIG. 10A is a schematic partially transparent view of an implant including an extra-luminal choke ring.
Figure 10B:
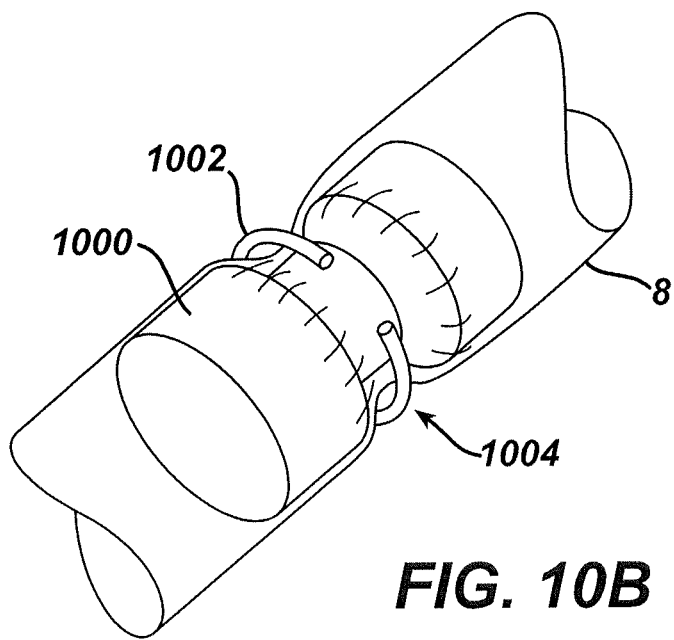
FIG. 10B is a schematic partially transparent view of an implant including an extra-luminal choke ring that is crimped.

FIGS. 10A and 10B are schematic partially transparent views of an implant 1000 including extraluminal choke ring 1002. In the embodiment illustrated in FIG. 10A, implant 1000 is implanted at a target location within intestine 8 and a choke ring 1002 is positioned extraluminally proximate a groove 1004. In FIG. 10B, choke ring 1002 is crimped such that it fits within groove 1004 in a manner that secures implant 1000 in place within intestine 8, yet prevents necrosis. Although illustrated as a round wire, it is contemplated that choke ring 1002 may be formed in different configurations to include features such as flat or undulating cross-sections, locking features, and the like, without departing from the scope of the present invention. Further, it is contemplated that this system may be implanted using non-invasive or minimally invasive methods such as single site laparoscopy.

Figure 11:
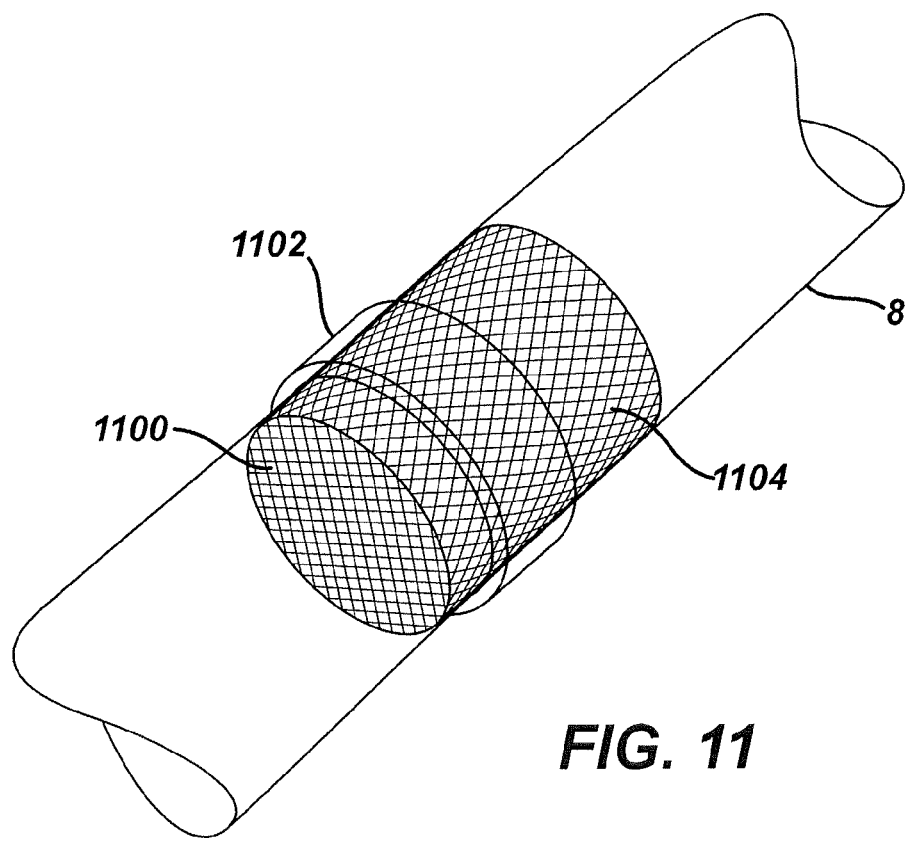
FIG. 11 is a schematic partially transparent view of an implant including a wide band choke ring.

FIG. 11 is a schematic partially transparent view of an implant 1100 including a wide band choke ring 1102. In this particular embodiment, implant 1100 is positioned within intestine 8 in a similar manner to that of the embodiment described above in FIGS. 8A and 8B. However, in this particular embodiment the external surface 1104 of implant 1100 does not include a groove and is formed of a mesh material. The mesh material comprising external surface 1104 causes numerous contact points between wide band choke ring 1102 and implant 1100 through intestine 8, thereby securing implant 1100 within intestine 8.

Figure 12:
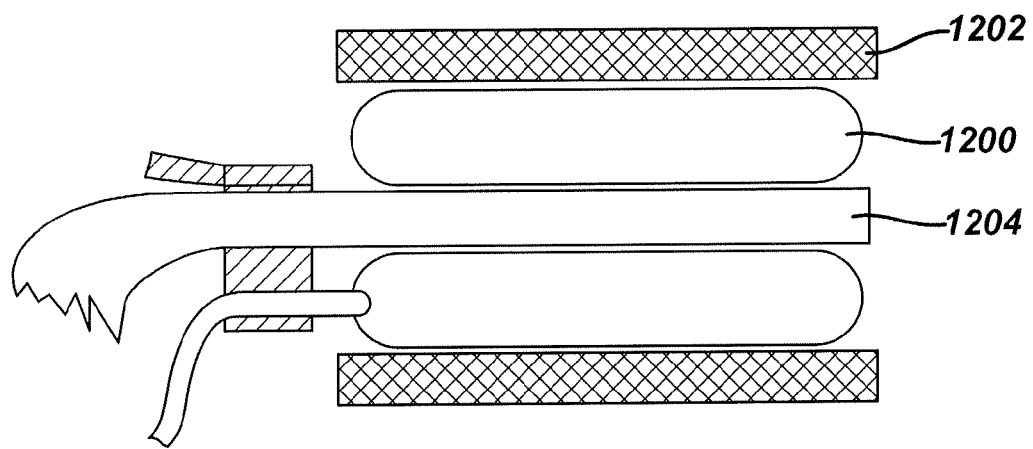
FIG. 12 is a schematic view of an inflatable delivery mechanism.

FIG. 12 is a schematic view of an inflatable delivery mechanism 1200. Mechanism 1200 is an exemplary means for delivering an implantable device such as stent 1202 into the GI tract as is detailed in previous embodiments of the present invention. In one embodiment, mechanism 1200 attaches to a flexible endoscope 1204 and mechanism 1200 is inflated to secure stent 1202 externally thereon. When stent 1202 is delivered to the desired location, mechanism 1200 is deflated thereby releasing stent 1202. At that point, mechanism 1200 and endoscope 1204 can be removed from the patient's body and mechanism 1200 can be removed from endoscope 1204. In an alternative embodiment, mechanism 1200 may stay in place with stent 1202 to serve as a reservoir of therapeutic substance. This would obviate the need to perform a separate fill procedure in situ upon deployment. It should be noted that implantation of a device within the GI tract may necessitate a guide wire extending means in order to reach the target area within the GI tract, since such locations typically fall beyond the ileocecal valve and thus may be out of reach for known colonoscopes.

Figure 13A:
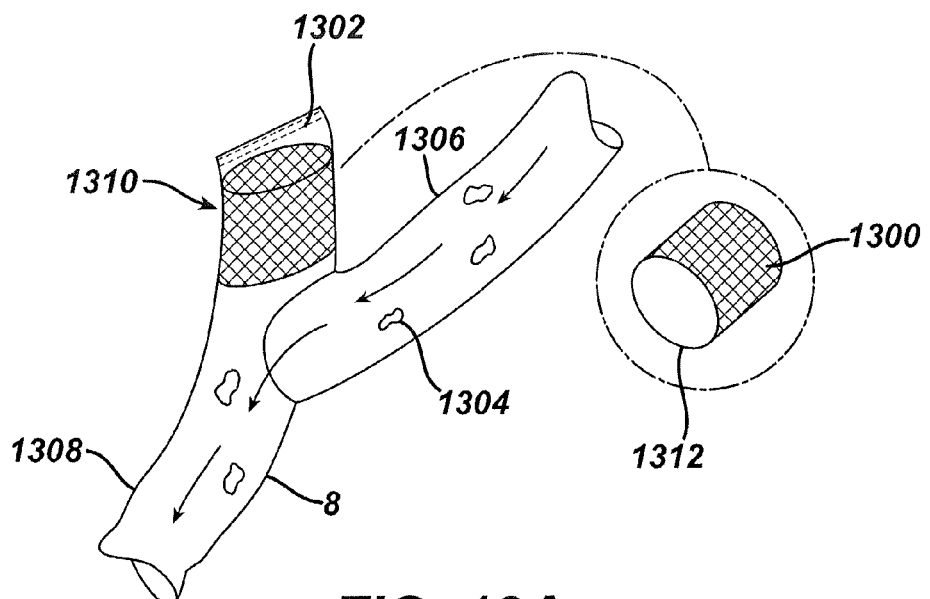
FIG. 13A is a schematic partially transparent view of artificially formed dead end branches for stabilizing an implant.
Figure 13B:
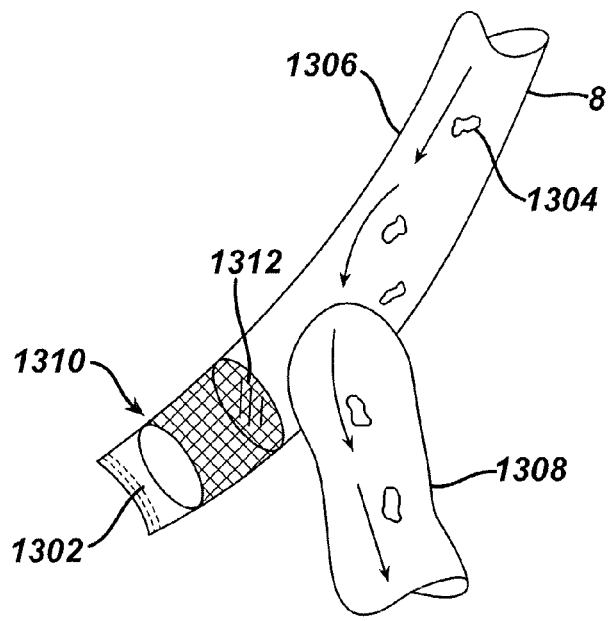
FIG. 13B is a schematic partially transparent view of artificially formed dead end branches for stabilizing an implant.

FIGS. 13A and 13B are schematic partially transparent views of artificially formed dead end branches for stabilizing an implant 1300. As is shown in FIGS. 13A and 13B, intestine 8 is transected at a location 1302, and an end-to-side anastomosis is performed in order to reconnect proximal portion 1306 and distal portion 1308 of intestine 8, thus leaving a branch portion 1310 in place with an implant 1300 therein. Branch 1310 and implant 1300 together serve as a retrograde dead end within intestine 8. Alternatively, a side-to-side anastomosis may be performed in place of the end-to-side anastomosis disclosed, so long as care is taken to prevent formation of a second blind pouch which may collect chyme. In either procedure, intestine 8 remains vascularized and connected to mesentery. Thus, implant 1300 may continue to have an impact on hormonal activities of intestine 8. Certain embodiments of implant 1300 may include an occluded end portion 1312 in order to prevent any chyme passage. As may be appreciated, implant 1300 may be of the drug eluting type disclosed previously herein. As yet another alternative, intestine 8 may undergo an end-to-end anastomosis in order to form a continuous section. Details of the end-to-end anastomosis are given in FIGS. 15A, 15B and 15C.

Figure 14A:
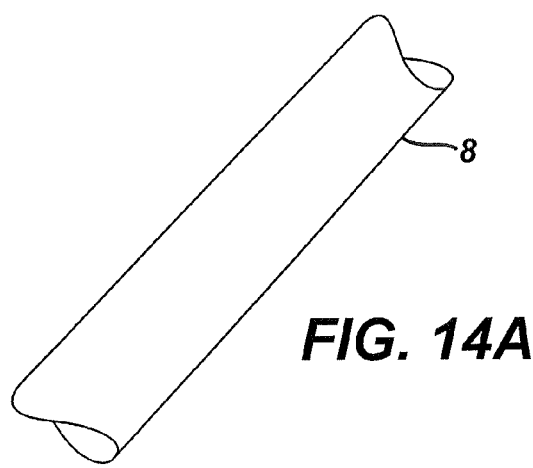
FIG. 14A is a schematic partially transparent view of a procedure for forming an artificial dead end branch prior to end-to-side anastomosis.
Figure 14B:
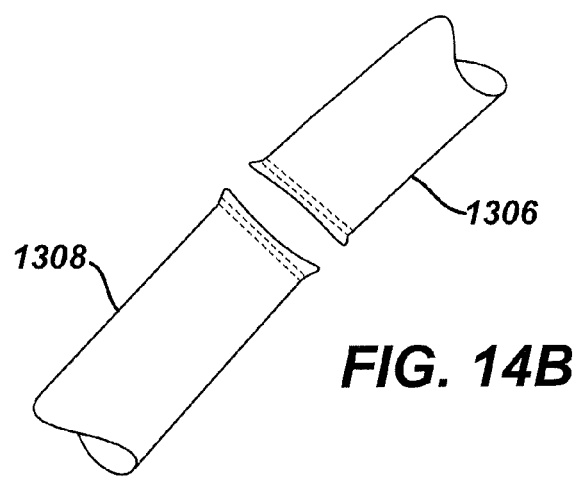
FIG. 14B is a schematic partially transparent view of a procedure for forming an artificial dead end branch when an intestine is transected.
Figure 14C:
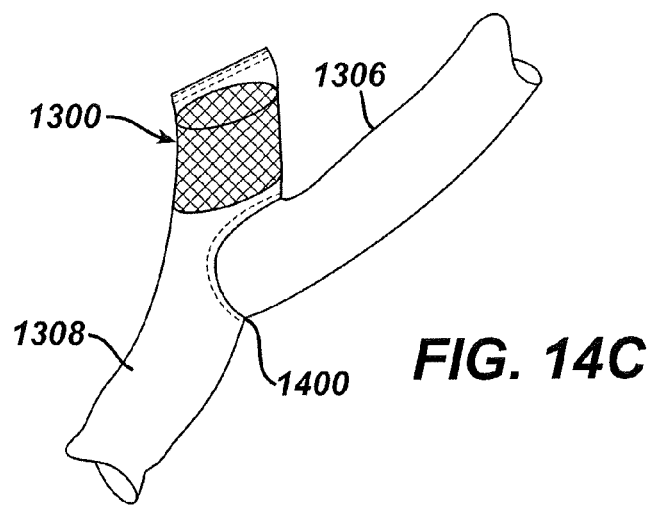
FIG. 14C is a schematic partially transparent view of a procedure for forming an artificial dead end branch via implantation.

FIGS. 14A, 14B and 14C are schematic partially transparent views of a procedure for forming an artificial dead end branch. FIGS. 14A, 14B and 14C outline the procedural steps for forming an artificial dead end branch as described in FIGS. 13A and 13B. FIG. 14A illustrates intestine 8 prior to end-to-side anastomosis. FIG. 14B illustrates intestine 8 transected into proximal portion 1306 and distal portion 1308 by means of a linear cutting device (not shown). FIG. 14C illustrates the formation of a dead end branch via implantation of implant 1300 and end-to-side anastomosis at junction 1400.

Figure 15A:
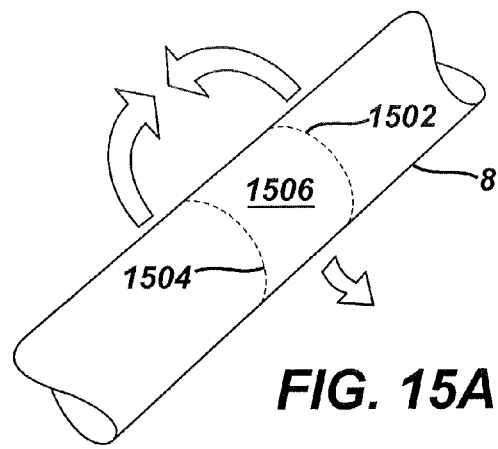
FIG. 15A is a schematic view of an intestine having cut lines shown.
Figure 15B:
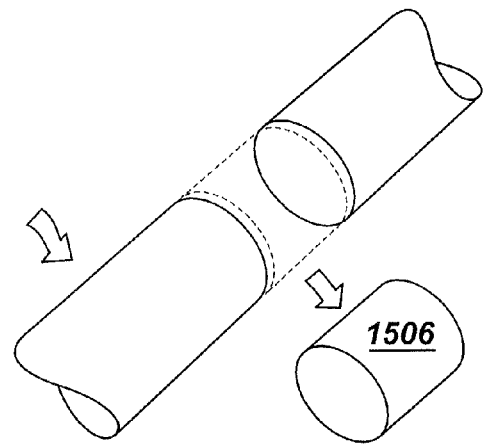
FIG. 15B is a schematic view of a portion of the intestine being excised.
Figure 15C:
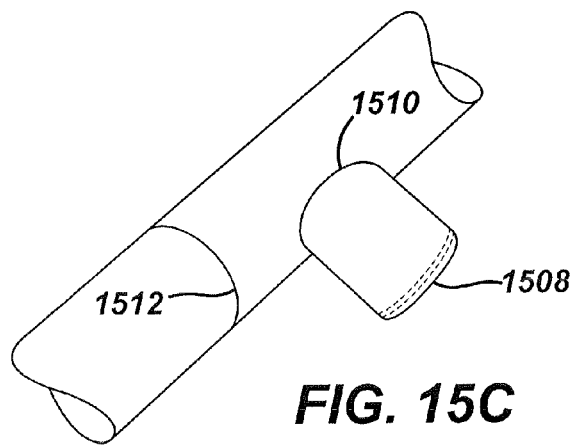
FIG. 15C is a schematic view of an artificially formed T-branch dead end for stabilizing an implant.

FIGS. 15A, 15B and 15C are schematic views of an artificially formed T-branch dead end for stabilizing an implant. FIGS. 15A, 15B and 15C outline the procedural steps for forming an artificially formed T-branch dead end for stabilizing an implant via an end-to-end anastomosis as was briefly mentioned in the description of alternative embodiments of FIGS. 13A and 13B. FIG. 15A illustrates intestine 8 having cut lines 1502 and 1504 shown therein. Together, cut lines 1502 and 1504 serve to create portion 1506 of intestine 8, which is shown to be excised in FIG. 15B. FIG. 15C illustrates the formation of an artificially formed T-branch dead end for stabilizing an implant (not shown) where excised portion 1506 is reattached to intestine 8 at junction 1510 and stapled at its opposing end to create a dead end branch 1508. Further, cut lines 1502 and 1504 are connected to form an end-to-end anastomosis 1512.

Figure 16D:
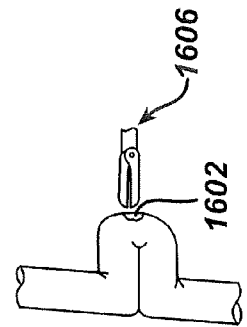
FIG. 16D is a schematic partially transparent view illustrating a fourth step for creating a dead end branch.
Figure 16C:
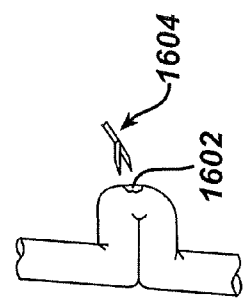
FIG. 16C is a schematic partially transparent view illustrating a third step for creating a dead end branch.
Figure 16B:
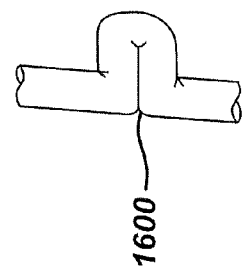
FIG. 16B is a schematic partially transparent view illustrating a second step for creating a dead end branch.
Figure 16A:
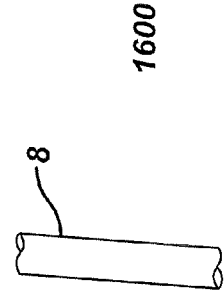
FIG. 16A is a schematic partially transparent view illustrating a first step for creating a dead end branch using proven laparoscopic stapler techniques.
Figure 16H:
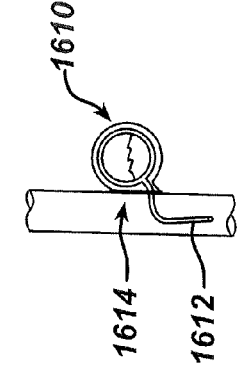
FIG. 16H is a schematic partially transparent view illustrating a eighth step for creating a dead end branch.
Figure 16G:
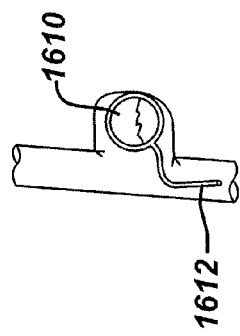
FIG. 16G is a schematic partially transparent view illustrating a seventh step for creating a dead end branch.
Figure 16F:
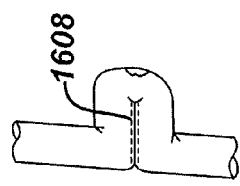
FIG. 16F is a schematic partially transparent view illustrating a sixth step for creating a dead end branch.
Figure 16E:
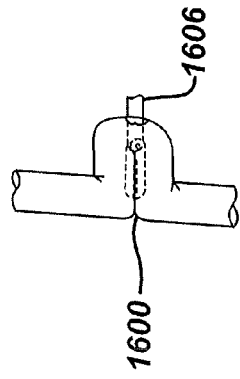
FIG. 16E is a schematic partially transparent view illustrating a fifth step for creating a dead end branch.

FIGS. 16A, 16B, 16C, 16D, 16E, 16F, 16G, and 16H are schematic partially transparent views illustrating the steps for creating a dead end branch using laparoscopic stapler techniques. A first step shown in FIG. 16A, illustrates intestine 8 in an unaffected state. In a second step shown in FIG. 16B, intestine 8 is folded to create an overlap 1600. In a third step shown in FIG. 16C, access is gained via aperture 1602 which is formed by cutting tool 1604. In a fourth step shown in FIG. 16D, stapler 1606 is inserted into folded intestine 8 through aperture 1602. In a fifth step shown in FIG. 16E, stapler 1606 secures overlap 1600 together with staples 1608. In a sixth step shown in FIG. 16F, stapler 1606 is removed through aperture 1602 and staples 1608 hold overlap 1600 together. In a seventh step shown in FIG. 16G, a therapeutic substance reservoir 1610 with a slow drip catheter portion 1612 is inserted into intestine 8 through aperture 1602. In an eighth and final step shown in FIG. 16H, aperture 1602 is closed and an external ring clamp 1614 is applied between the tissue surrounding reservoir 1610 and the remainder of intestine 8 such that reservoir 1610 is maintained within the dead end branch portion formed and catheter 1612 is positioned in the flow path of intestine 8 in order to provide a slow drip therapeutic substance which will initiate an intestinal braking effect and thereby create or maintain a sensation of satiety in the patient.

Figure 17D:
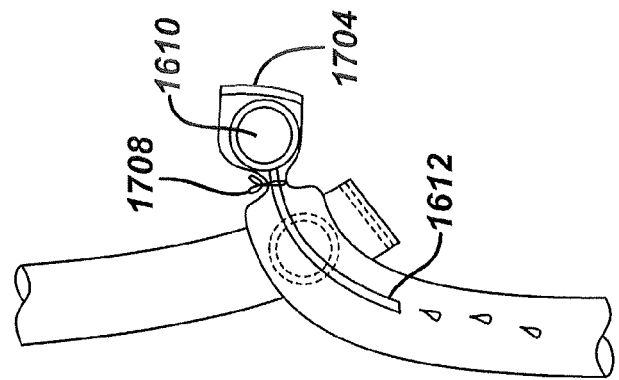
FIG. 17D is a schematic partially transparent view illustrating a fourth step for creating a dead end and holding an implant within the dead end using a linear stapler, circular stapler and an extra-luminal band.
Figure 17C:
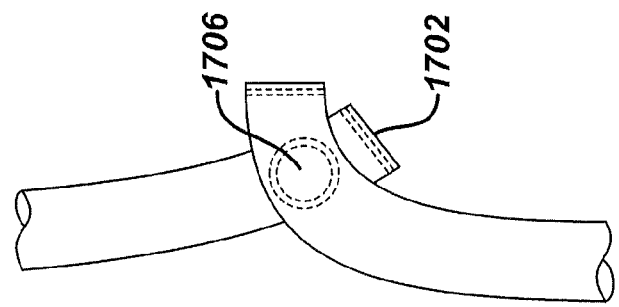
FIG. 17C is a schematic partially transparent view illustrating a third step for creating a dead and holding an implant within the dead end using a linear stapler, circular stapler and an extra-luminal band.
Figure 17B:
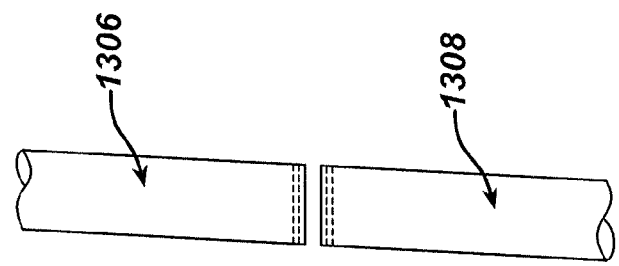
FIG. 17B is a schematic partially transparent view illustrating a second step for creating a dead end and holding an implant within the dead end using a linear stapler, circular stapler and an extra-luminal band.
Figure 17A:
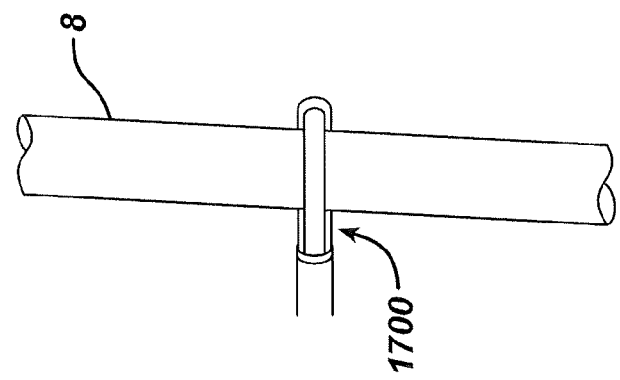
FIG. 17A is a schematic partially transparent view illustrating a step for creating a dead end and holding an implant within the dead end using a linear stapler, circular stapler and an extra-luminal band.

FIGS. 17A, 17B, 17C, and 17D are schematic partially transparent views illustrating the steps for creating a dead end and holding an implant 1610 within the dead end using a linear stapler, circular stapler and an extraluminal band. FIG. 17A and FIG. 17B illustrate intestine 8 being transected into proximal portion 1306 and distal portion 1308 by means of a linear cutting device 1700. In a third step shown in FIG. 17C, proximal portion 1306 of intestine 8 is stapled at its transected end to create a dead end, and a side-to-side anastomosis 1706 is performed to reconnect proximal portion 1306 and distal portion 1308. In a forth and final step shown in FIG. 17D, a therapeutic substance reservoir 1610 with a slow drip catheter portion 1612 is inserted into intestine 8 through open transected end 1704 of distal portion 1308 of intestine 8, which is then stapled closed and an external ring clamp 1708 is applied between the tissue surrounding reservoir 1610 and the remainder of intestine 8 such that reservoir 1610 is maintained within the dead end branch portion formed and catheter 1612 is positioned in the flow path of intestine 8 in order to provide a slow drip therapeutic substance which will initiate an intestinal braking effect and thereby create or maintain a sensation of satiety in the patient.

Figure 18A:
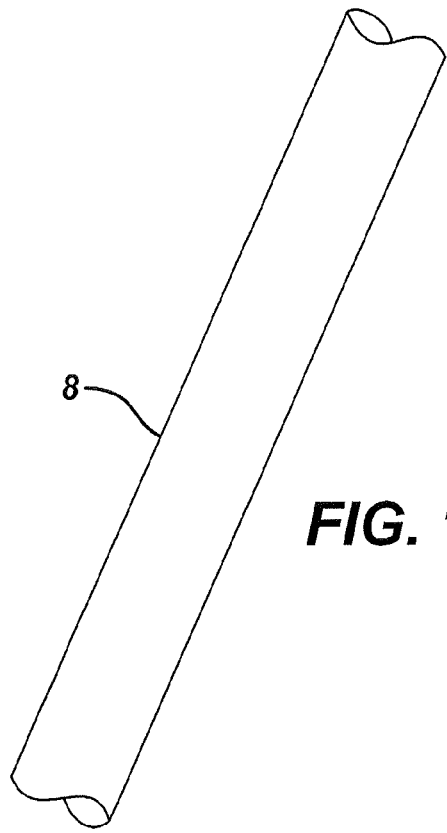
FIG. 18A is a schematic partially transparent view of a loop anastomosis for stabilizing an implant.
Figure 18B:
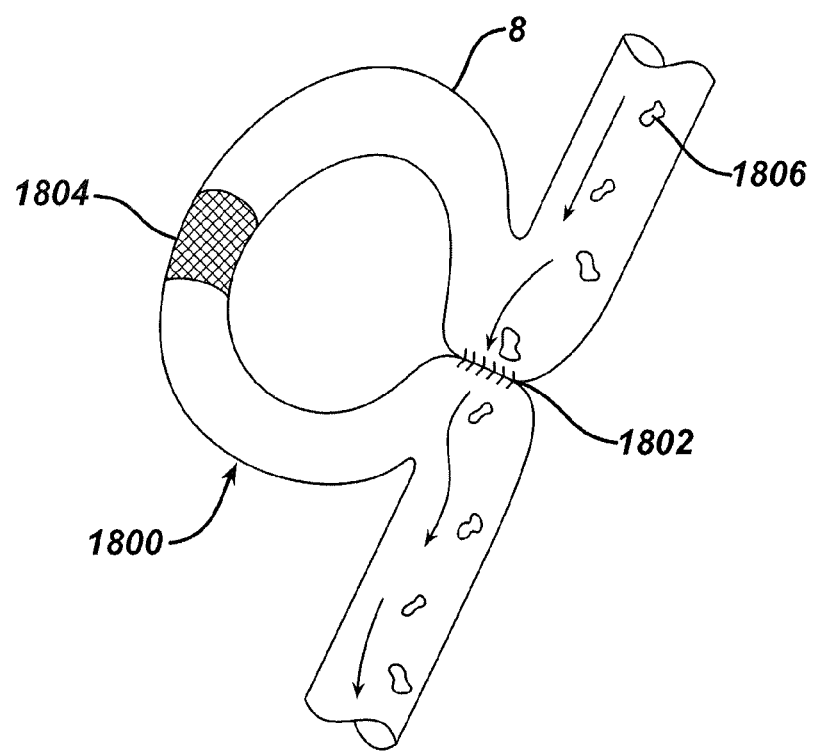
FIG. 18B is a schematic partially transparent view of a loop anastomosis for stabilizing an implant.

FIGS. 18A and 18B are schematic partially transparent views of a loop anastomosis for stabilizing an implant 1804. FIG. 18A illustrates intestine 8 prior to loop anastomosis. FIG. 18B illustrates wherein a loop 1800 is formed by bringing two distal points of intestine 8 together with a side-to-side anastomosis 1802 having flow channels therethrough though which chyme 1806 passes. In this manner, loop 1800 houses implant 1804 thereby keeping it from the chyme path, yet allowing it to initiate an intestinal braking effect in intestine 8 as with previously disclosed embodiments of the present invention. In some embodiments, occluded implants may be further provided to prevent chyme 1806 from entering loop 1800 which may cause blockage or infection.

Figure 19A:
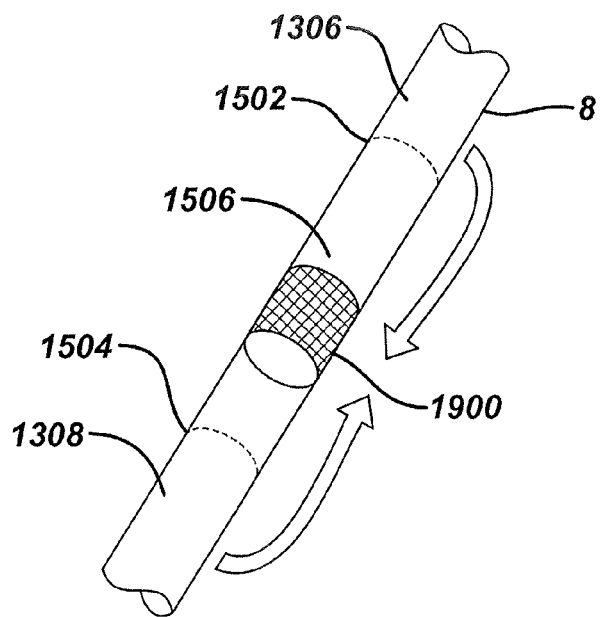
FIG. 19A is a schematic partially transparent view of a minimal segment loop for stabilizing an implant.
Figure 19B:
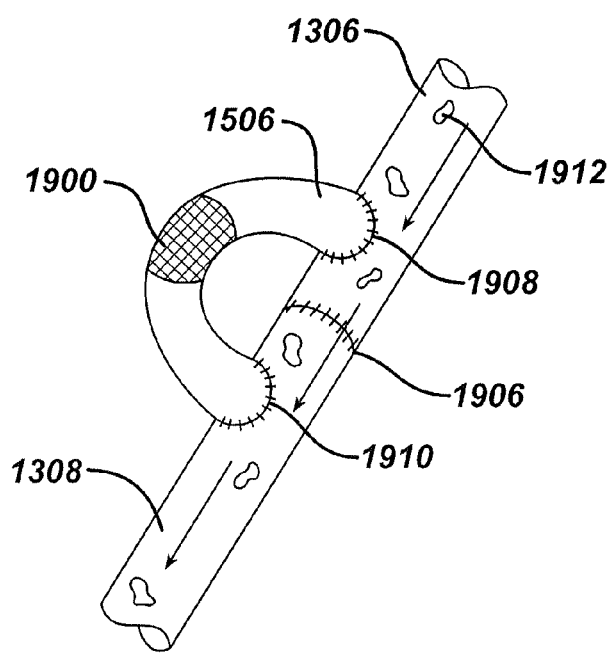
FIG. 19B is a schematic partially transparent view of a minimal segment loop for stabilizing an implant.

FIGS. 19A and 19B are schematic partially transparent views of a minimal segment loop for stabilizing an implant 1900. FIG. 19A illustrates intestine 8 having implant 1900 positioned therein and cut lines 1502 and 1504 thereon, prior to loop anastomosis. Together, cut lines 1502 and 1504 serve to define proximal portion 1306 and distal portion 1308 and further to create portion 1506 of intestine 8, which is shown to be excised and reattached via loop anastomosis in FIG. 19B. FIG. 19B illustrates the completed loop anastomosis procedure wherein excised intestine portion 1506 serves as a loop which is attached to intestine 8 at end 1908 and end 1910 via end-to-side anastomosis. Further, cut lines 1502 and 1504 are brought together at junction 1906 via end-to-end anastomosis. In this manner, the loop formed by portion 1506 houses implant 1900 thereby keeping it from the chyme path, yet allowing it to initiate an intestinal braking effect in intestine 8 as with previously disclosed embodiments of the present invention. In some embodiments, occluded implants may be further provided to prevent chyme 1912 from entering the loop formed by portion 1506 which may cause blockage or infection.

Figure 20:
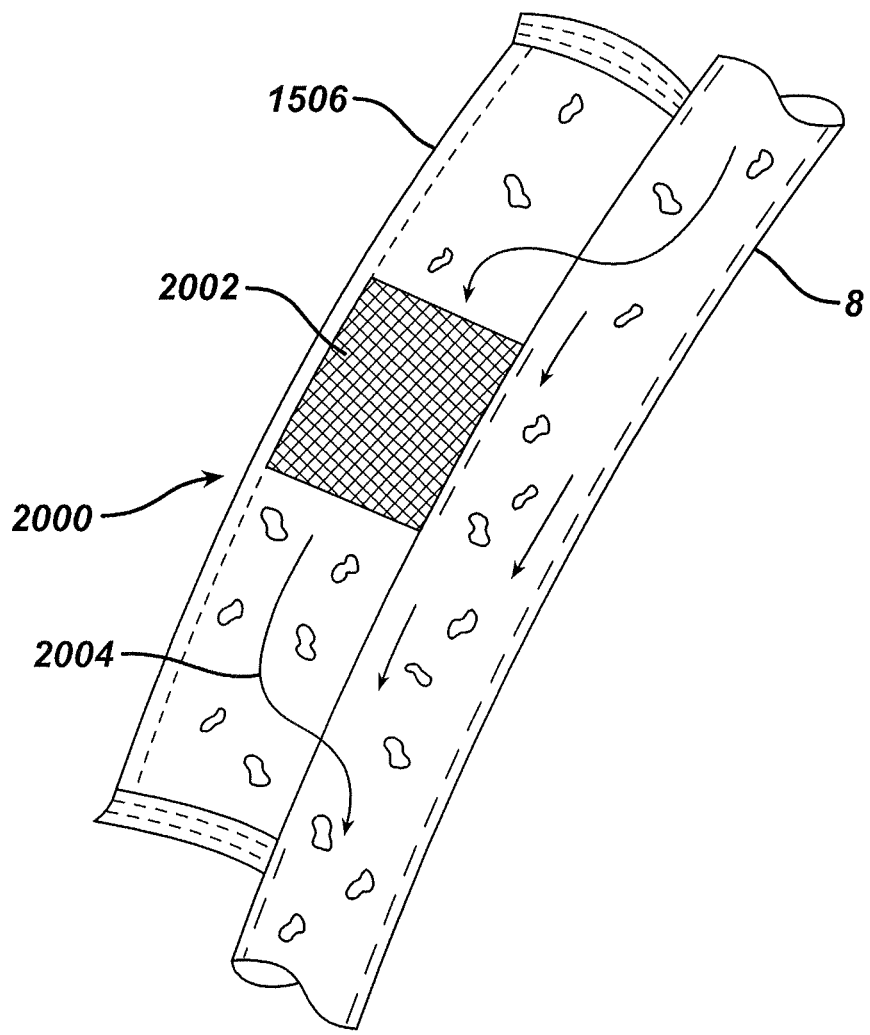
FIG. 20 is a schematic partially transparent view of an excised portion of intestine reattached to the intestine via side-to-side anastomosis thereby creating a flow through chyme pouch having an implant therein.

FIG. 20 is a schematic partially transparent view of an excised portion 1506 of intestine 8 reattached to the intestine via side-to-side anastomosis thereby creating a flow through chyme pouch 2000 having an implant 2002 therein. As was disclosed previously herein with respect to other embodiments, implant 2002 may be of the flow through and/or slow drip type and may further have therapeutic substance eluting properties in order to initiate a desired intestinal braking effect. As an alternative, implant may be of the sponge type as was discussed previously herein in regard to FIG. 9, wherein peristalsis moves chyme through the GI tract, such that some chyme contained within the sponge material of implant 2002 is pushed out, and flows in a direction indicated by arrow 2004. Subsequent peristaltic motions repeat this effect. Therefore, some amount of chyme is delayed from movement through the GI tract, thereby creating a prolonged sensation of satiation in a patient.

Figure 21:
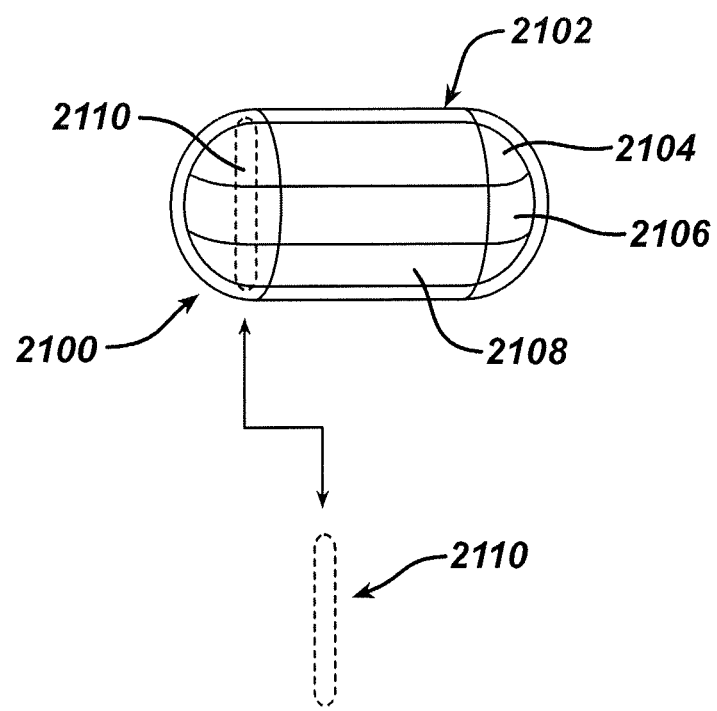
FIG. 21 is a schematic partially transparent view of an ingestible eluting device in its collapsed form.

FIG. 21 is a schematic partially transparent view of an ingestible eluting device 2100 in its collapsed form. In one embodiment, device 2100 has a short term degradable exterior coating 2102 which contains three collapsed pill sections 2104, 2106 and 2108, as well as an axle 2110 therein. In one embodiment, axle 2110 is formed of a bioabsorbable polymer. Further, pill sections 2104, 2106 and 2108 may be formed of one or more types of therapeutic substance. In another embodiment, device 2100 may contain apertures which allow passage of chyme and the like therethrough. As may be appreciated, device 2100 may take on any number of sizes and shapes, but in certain embodiments device 2100 is sized and shaped such that it cannot pass through the ileocecal valve without undergoing degradation of its degradable components.

Figure 22:
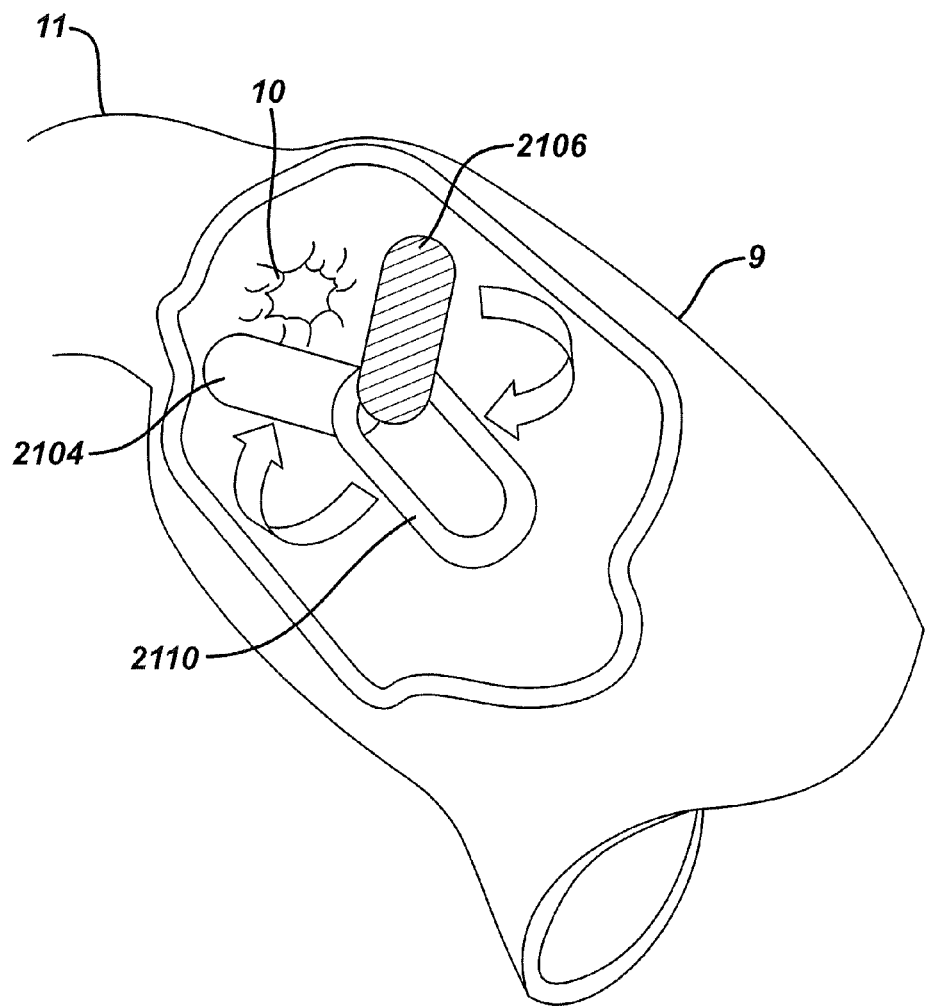
FIG. 22 is a schematic partially transparent view of an ingestible eluting device in its expanded form.

FIG. 22 is a schematic partially transparent view of the ingestible eluting device 2100 in its expanded form. In this particular embodiment, pill sections 2104 and 2106, and axle 2110 are shown expanded radially from a center point at angles of roughly 120° from one another, although other angles are anticipated depending upon factors such as the number of pill layers in device 2100. As may be seen in FIG. 22, none of the components of device 2100 are permitted to block passage of chyme and other substances through ileocecal valve 10 due to their radially expanded configuration. As was discussed previously herein, device 2100 is sized and shaped such that it cannot pass from ileum 9 to large intestine 11 through ileocecal valve 10 without undergoing degradation of its degradable components. However, once the degradable components of device 2100 have become depleted, the remaining components may then pass through ileocecal valve 10 and through the remainder of the GI tract naturally.

Figure 23A:
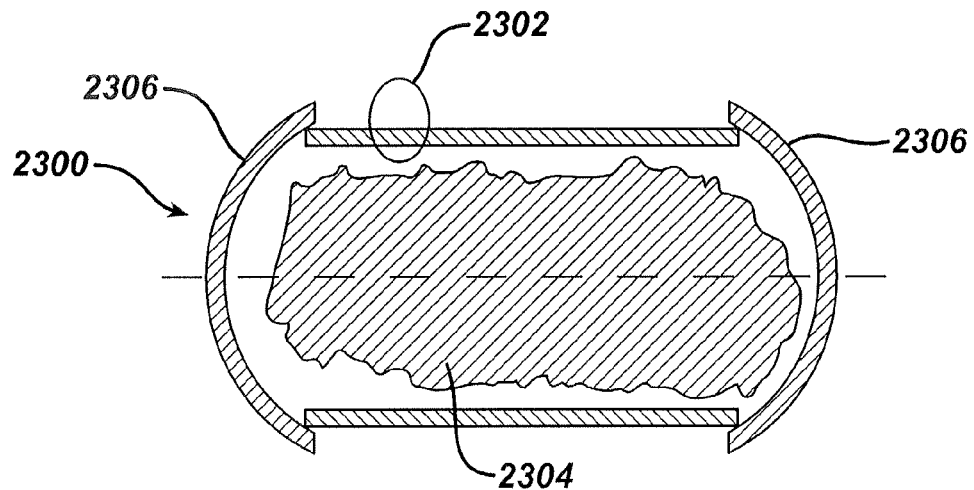
FIG. 23A is a cross-sectional view of a therapeutic substance pill.
Figure 23B:
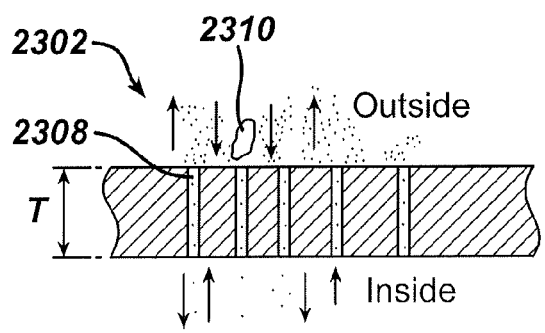
FIG. 23B is a schematic partially transparent view of a therapeutic substance pill with nanochannels and details thereof.
Figure 23C:
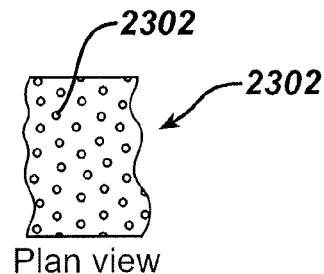
FIG. 23C is a partial plan view of a therapeutic substance pill with nanochannels and details thereof.

FIG. 23A and 23B are schematic partially transparent views of a therapeutic substance pill 2300 with nanochannels 2308 and details thereof. FIG. 23A illustrates a cross-sectional view of pill 2300 having sidewall 2302 and end caps 2306 containing a therapeutic substance 2304 therein. In this particular embodiment, therapeutic substance 2304 comprises fat or glucose, although numerous other therapeutic substances may be utilized in addition to or in place of fat or glucose. In certain embodiments, therapeutic substance 2304 acts to stimulate GLP-1 over a short period of time as it passes by K-cells within the duodenum and then again stimulating GLP-1 through the L-cells within the ileum in order to induce an intestinal braking effect. The principle being triggering the signaling pathway for GLP-1 stimulation without the negative effects associated with ingesting additional fat or glucose. As can be seen in FIGS. 23B and 23C, sidewall 2302 has a thickness T through which nanochannels 2308 pass. Nanochannels 2308 may be patterned and sized as desired to enable the desired amount of fluid communication therethrough, and may further serve as an enzyme barrier to prevent digestion of therapeutic substance 2304 contained within pill 2300, but still allow for the passage of GLP-1 which would allow the body's signaling pathway to identify the presence of therapeutic substance 2304 in the GI tract in order to stimulate GLP-1. In certain embodiments, sidewall 2302 may be constructed of polymeric material or of silicon. In certain other embodiments, an adhesive may coat a portion of pill 2300 thereby allowing it to be easily secured in a desired location within the GI tract.

Figure 24A:
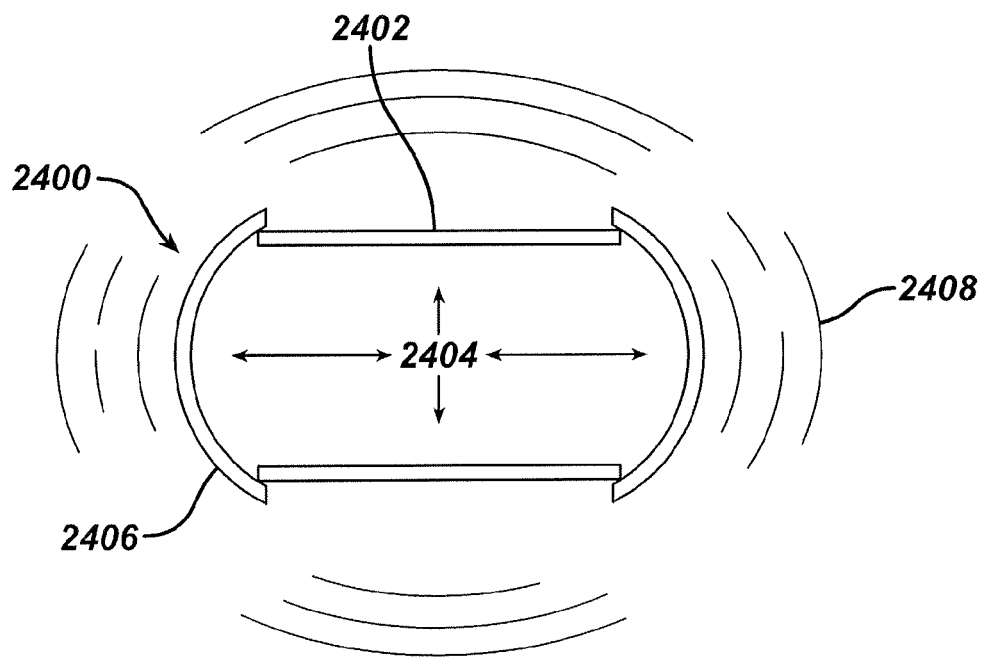
FIG. 24A is a cross-sectional view of a pressure wave pill.
Figure 24B:
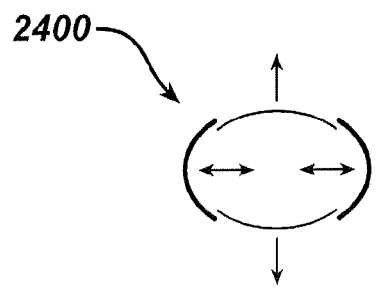
FIG. 24B is a schematic partially transparent view of a pressure wave pill and details thereof.

FIGS. 24A and 24B are schematic partially transparent views of a pressure wave pill 2400 and details thereof. FIG. 24A illustrates a cross-sectional view of pill 2400 having sidewall 2402 and end caps 2406 containing therein an electromechanical system 2404 for creating pulse waves 2408. In this particular embodiment, sidewall 2402 is formed of a semi-flexible material that allows outward expansion, as is shown in FIG. 24B, which aids in the production of pulse waves 2408. The creation of pulse waves 2408 may be done for example by generating a low frequency pressure wave using electromechanical system 2404 which, if done in the ileum, would stimulate the interaction of chyme with the villi and microvilli, and thus with the L-cells of the ileum. Such stimulation would in turn initiate an intestinal braking effect creating a sensation of satiation in the patient. In certain embodiments, electromechanical system 2404 may consist of a MEMS transducer that would be capable of creating an abrupt expansion of sidewall 2402 which would in turn propagate pulse waves 2408 through the chyme within the immediate proximity of pill 2400. As may be appreciated, pill 2400 may contain its own power source and be activated in the stool, or may be a passive type device. Further, additional coatings and barrier layers that may affect the travel rate and/or chemical/hormonal characteristics of pill 2400 are also contemplated. As with previous embodiments of the present invention, pill 2400 may also deliver a therapeutic substance if so desired.

Figure 25:
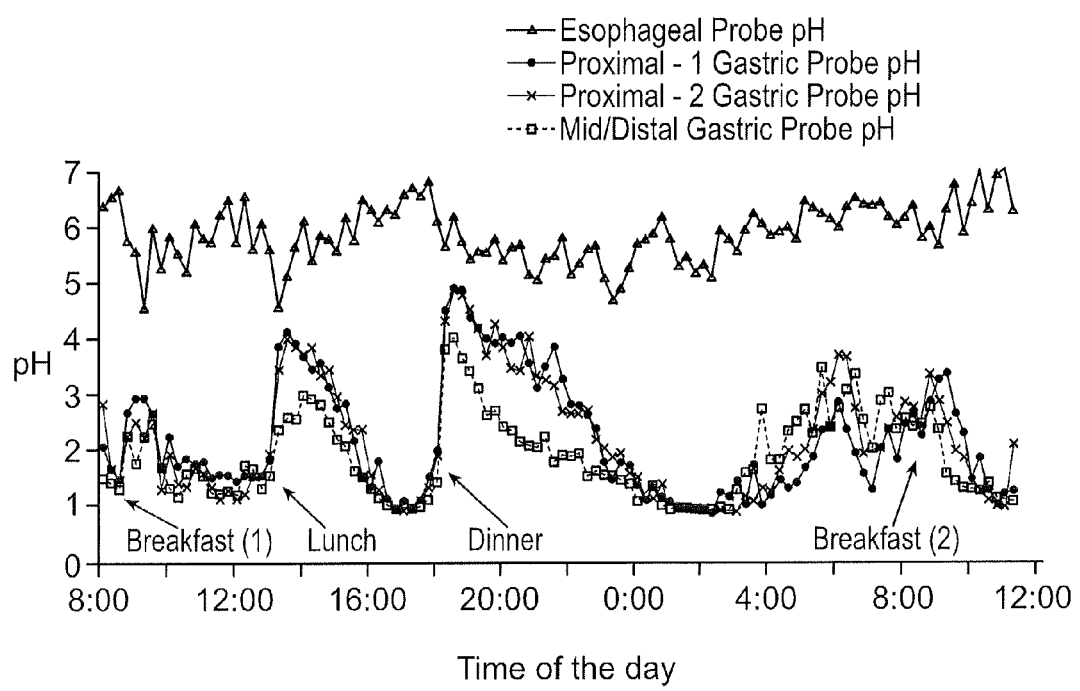
FIG. 25 is a graph representing pH changes in a patient's stomach throughout the day.

FIG. 25 is a graph representing pH changes in a patient's stomach throughout the day, as taken from Simonian, H. P., Vo, L., Doma, S., Fisher, R. S., Parkman, H. P., "Regional Postprandial Differences in pH within the Stomach and Gastroesophageal Junction", Digestive Diseases and Sciences, pgs. 2276-2285; 50(12) 2005. As may be seen from this graph, physiological changes of the digestive system between fasting and consumption may be described in terms of changes in gastric acidity as measured using pH (the log concentration of hydronium ion concentration, or log [H+]).

The pH scale spans from 1 (acidic) to 14 (basic), with 7.0 being neutral. During the fasting state, the stomach pH is low (acidic). With meal ingestion, there is buffering of intragastric acidity with an elevation of gastric pH. The change in pH occurs rapidly with the initiation of consumption as food enters into the stomach. This change also occurs even in light of the secretion of gastric acids continuously during consumption. The buffering capacity of foods, including acidic or "spicy" foods is sufficient to provide a significant change in gastric pH.

In regards to the information disclosed in the graph of FIG. 25, it is desirable to treat a patient with a pill which creates a coating within the stomach that helps to induce an intestinal braking effect. In one embodiment, such a pill would accelerate the delivery of fatty acid compounds and/or other therapeutic substances to the body to enable a reduction in food consumption or the sensation of hunger in a patient. In one embodiment, when such a pill is ingested, chemical compounds which terminate in long chain fatty acids are contained within the pill and act to bind to the interior walls of the stomach at acidic pH levels. Upon initial consumption of a meal, compounds release which act to neutralize the pH levels in the stomach. The bound chemical compounds are then released from the stomach walls into the stomach in high concentrations at the start of the meal, thus allowing for a more rapid stimulation of the ileum to initiate an intestinal braking effect. It may be desirable to include longer chained fatty acids such as palmitic, lignoceric acid, and hexacosanic acid in order to decrease the digestibility of the substance, thereby increasing the likelihood that the substance reaches the ileum.

Figure 26B:
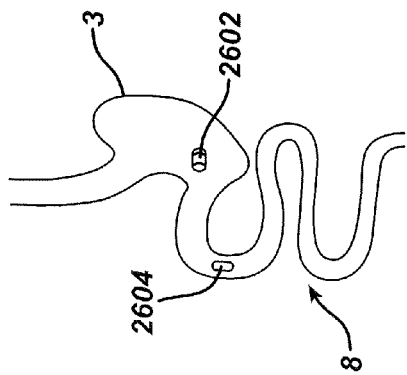
FIG. 26B is a schematic partially transparent view showing the progression of a pill to increase peristalsis as it passes through the stomach and intestines of a patient.
Figure 26E:
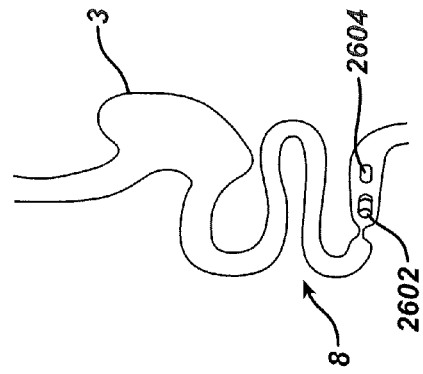
FIG. 26E is a schematic partially transparent view showing the progression of a pill to increase peristalsis as it passes through the stomach and intestines of a patient.
Figure 26A:
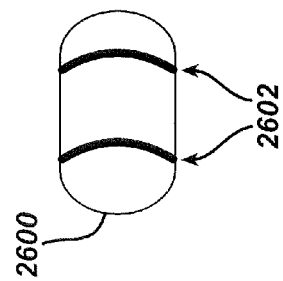
FIG. 26A is an illustration of a second pill in a two pill system.
Figure 26D:
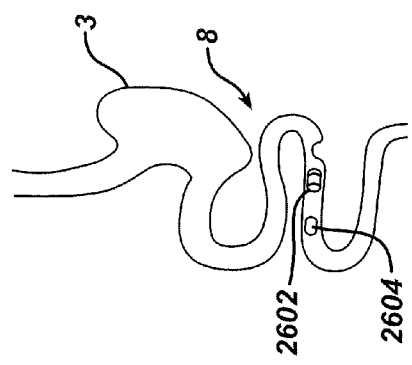
FIG. 26D is a schematic partially transparent view showing the progression of a pill to increase peristalsis as it passes through the stomach and intestines of a patient.
Figure 26C:
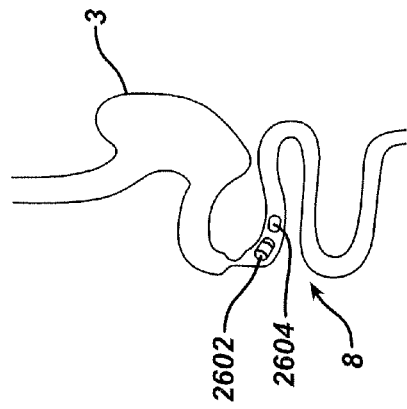
FIG. 26C is a schematic partially transparent view showing the progression of a pill to increase peristalsis as it passes through the stomach and intestines of a patient.

FIGS. 26A, 26B, 26C, 26D, and 26E are schematic partially transparent views of a pill 2600 to increase peristalsis as it passes through stomach 3 and intestines 8 of a patient. FIG. 26A illustrates the second pill 2600 of a two pill system. In one embodiment, a first pill 2604 comprising a nutrient pill having a degradable outer layer is ingested orally by a patient. A short time later, second pill 2600 is ingested orally. In certain embodiments, pill 2600 is an electronic pill having low voltage electrodes 2602 thereon. In such embodiments, electrodes 2602 are pulsed to create an increase in the peristaltic rate of the GI tract. FIGS. 26B, 26C, 26D, and 26E show the progression of nutrient pill 2604 and electronic pill 2600 through the GI tract utilizing the increased peristalsis created by electronic pill 2600 as a means to speed delivery of the pills to the target location. As may be appreciated, alternative embodiments may comprise a combined electronic and nutrient pill, or may utilize other known means for increasing peristalsis.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

We claim:

1. A method of producing satiety in a patient, the method comprising the steps of:
   a. accessing a gastrointestinal tract of the patient;
   b. implanting an intraintestinal therapeutic substance eluting implant in an ileum of the gastrointestinal tract; wherein said intraintestinal therapeutic substance implant comprises a satiety inducing substance selected from at least one of a nutrient, a specific satiety inducing bio-active substance, pancreatic polypeptides, free fatty acids, cholecystokinin, amino acids, glutamine, lipids, linoleic acid, or a combination thereof; and
   c. positioning a choke ring extraluminally of the ileum proximate to the implant;
   wherein said intraintestinal therapeutic substance eluting implant is configured to administer said satiety inducing substance into the gastrointestinal tract;
   wherein said intraintestinal therapeutic substance implant releases said satiety inducing substance after said act of implanting;
   wherein there is no anatomical change to said gastrointestinal tract.

2. The method of claim 1 wherein said intraintestinal therapeutic substance eluting implant comprises absorbent material.

3. The method of claim 1 wherein said intraintestinal therapeutic substance eluting implant comprises a degradable material that degrades in about one year after implantation.

4. The method of claim 1 wherein said intraintestinal therapeutic substance eluting implant releases said satiety inducing substance in a pulsating manner.

5. The method of claim 1 wherein said intraintestinal therapeutic substance eluting implant comprises a pressure sensing system, wherein said pressure sensing system is positioned at a cardia of said patient, and wherein ingestion of food by said patient is registered as a signal by said pressure sensing system, said signal being capable of initiating release of said substance from said intestinal therapeutic substance eluting implant.

6. The method of claim 1 wherein said intraintestinal therapeutic substance eluting implant comprises a layer of therapeutic substance containing polymer and a layer of non-therapeutic substance containing polymer.

7. The method of claim 1 wherein said intraintestinal therapeutic substance eluting implant comprises at least two layers comprising different doses of said at least one substance and/or at least two layers comprising one or more different substances.

8. The method of claim 1 wherein said intraintestinal therapeutic substance eluting implant delivers an electrical stimulation to said gastrointestinal tract and said satiety inducing substance comprises linoleic acid.

9. The method of claim 1 wherein said intraintestinal therapeutic substance eluting implant further comprises a fill port and is rechargeable.

10. The method of claim 1 wherein said intraintestinal therapeutic substance eluting implant comprises a chyme holding implant.

11. The method of claim 1 wherein said intraintestinal therapeutic substance eluting implant comprises a conical chyme pouch.

12. The method of claim 1 wherein said act of implanting said intraintestinal therapeutic substance eluting implant further comprises stabilizing said intraintestinal therapeutic substance eluting implant using dead end branches.

13. The method of claim 1 wherein said act of implanting said intraintestinal therapeutic substance eluting implant is performed during a colonoscopy.

14. A method of producing satiety in a patient, the method comprising the steps of:
   a. accessing a gastrointestinal tract of the patient;
   b. implanting an intraintestinal therapeutic substance eluting implant just past an ileocecal valve of the gastrointestinal tract; wherein said intraintestinal therapeutic substance implant comprises a satiety inducing substance selected from at least one of a nutrient, a specific satiety inducing bio-active substance, pancreatic polypeptides, free fatty acids, cholecystokinin, amino acids, glutamine, lipids, linoleic acid, or a combination thereof; and wherein said intraintestinal therapeutic substance eluting implant is configured to administer said satiety inducing substance into the gastrointestinal tract;

wherein said intraintestinal therapeutic substance implant releases said satiety inducing substance after said act of implanting;

wherein there is no anatomical change to said gastrointestinal tract.

15. The method of claim 14 wherein said intraintestinal therapeutic substance eluting implant comprises a degradable material that degrades in about one year after implantation.

16. The method of claim 14 wherein said intraintestinal therapeutic substance eluting implant comprises at least two layers comprising different doses of said at least one substance and/or at least two layers comprising one or more different substances.

17. A method of producing satiety in a patient, the method comprising the steps of:
 a. accessing a gastrointestinal tract of the patient;
 b. implanting an intraintestinal therapeutic substance eluting implant at an ileocecal valve of the gastrointestinal tract; wherein said intraintestinal therapeutic substance implant comprises a satiety inducing substance selected from at least one of a nutrient, a specific satiety inducing bio-active substance, pancreatic polypeptides, free fatty acids, cholecystokinin, amino acids, glutamine, lipids, linoleic acid, or a combination thereof; and wherein said intraintestinal therapeutic substance eluting implant is configured to administer said satiety inducing substance into the gastrointestinal tract; wherein said intraintestinal therapeutic substance implant releases said satiety inducing substance after said act of implanting;

wherein there is no anatomical change to said gastrointestinal tract;

wherein said intraintestinal therapeutic substance eluting implant is of a continuous cylindrical shape of a sufficient diameter to prevent passage of said intraintestinal therapeutic substance eluting implant through the ileocecal valve.

18. The method of claim 17 wherein said intraintestinal therapeutic substance eluting implant comprises a degradable material that degrades in about one year after implantation.

19. The method of claim 17 wherein said act of implanting said intraintestinal therapeutic substance eluting implant further comprises placing said intraintestinal therapeutic substance eluting implant at the ileum.

* * * * *